US009464010B2

(12) United States Patent
Naterer et al.

(10) Patent No.: US 9,464,010 B2
(45) Date of Patent: Oct. 11, 2016

(54) SYSTEMS, METHODS AND DEVICES FOR THE CAPTURE AND HYDROGENATION OF CARBON DIOXIDE WITH THERMOCHEMICAL CU—CL AND MG—CL—NA/K—CO2 CYCLES

(71) Applicant: UNIVERSITY OF ONTARIO INSTITUTE OF TECHNOLOGY, Oshawa (CA)

(72) Inventors: Greg Naterer, St-John's (CA); Zhaolin (Forest) Wang, Whitby (CA)

(73) Assignee: UNIVERSITY OF TORONTO INSTITUTE OF TECHNOLOGY, Oshawa, Ontario (CA)

(*) Notice: Subject to any disclaimer, the term of this patent is extended or adjusted under 35 U.S.C. 154(b) by 0 days.

(21) Appl. No.: 14/442,007

(22) PCT Filed: Nov. 12, 2013

(86) PCT No.: PCT/CA2013/000958
§ 371 (c)(1),
(2) Date: May 11, 2015

(87) PCT Pub. No.: WO2014/071511
PCT Pub. Date: May 15, 2014

(65) Prior Publication Data
US 2016/0039724 A1 Feb. 11, 2016

Related U.S. Application Data

(60) Provisional application No. 61/724,665, filed on Nov. 9, 2012.

(51) Int. Cl.
*B01J 8/00* (2006.01)
*B01J 8/18* (2006.01)
(Continued)

(52) U.S. Cl.
CPC ............ *C07C 1/12* (2013.01); *B01D 53/1425* (2013.01); *B01J 8/34* (2013.01); *C01C 1/0488* (2013.01);
(Continued)

(58) Field of Classification Search
CPC ............... B01J 8/00; B01J 8/18; B01J 8/24; B01J 8/34; B01J 2208/00796–2208/00814; B01D 53/00; B01D 53/04; B01D 53/14; B01D 53/1425; B01D 53/1456; B01D 53/1475; B01D 53/02; B01D 2257/50; B01D 2257/504; C07C 1/02; C07C 1/12; C07C 29/15; C07C 29/151; C07C 29/1516; C07C 29/1518; C07C 43/00; C07C 43/02; C07C 1/00; C01C 1/02; C01C 1/04; C01C 1/0405; C01C 1/0488; C01C 1/00; C25B 1/00; C25B 1/14; C25B 1/16; C25B 1/24; C25B 1/26
See application file for complete search history.

(56) References Cited

U.S. PATENT DOCUMENTS

| | | | |
|---|---|---|---|
| 2010/0025260 A1* | 2/2010 | Naterer | C01B 3/08 205/637 |
| 2010/0270167 A1* | 10/2010 | McFarland | C07C 1/26 205/462 |
| 2011/0041740 A1* | 2/2011 | Reilly | F23C 9/00 110/341 |

*Primary Examiner* — Natasha Young
(74) *Attorney, Agent, or Firm* — Equinox IP; Franz Bonsang

(57) ABSTRACT

Systems, methods, and devices for producing hydrogen and capturing CO2 from emissions combine both H2 production and CO2 capture processes in forms of thermochemical cycles to produce useful products from captured CO2. The thermochemical cycles are copper-chlorine (Cu—Cl) and magnesium-chlorine-sodium/potassium cycles (Mg—Cl—Na/K—CO2). One system comprises a Cu—Cl cycle, a CO2 capture loop, and a hydrogenation cycle. Another system comprises an Mg—Cl—Na/K—CO2 cycle and a hydrogenation cycle. Devices for hydrogen production, CO2 capture, hydrogenation, and process and equipment integration include a two-stage fluidized/packed bed, hybrid two-stage spray-fluidized/packed bed reactor, a two-stage wet-mode absorber, a hybrid two-stage absorber, and a catalyst packed/fluidized bed reactor.

30 Claims, 6 Drawing Sheets

Figure 1: Schematic of the Cu-Cl cycle with CO2 capture and hydrogenation (drying and hydrolysis processes of CuCl2 and absorption of CO2 are shown in separate apparatus)

(51) Int. Cl.
| | |
|---|---|
| *B01J 8/24* | (2006.01) |
| *B01J 8/34* | (2006.01) |
| *C25B 1/00* | (2006.01) |
| *C25B 1/14* | (2006.01) |
| *C25B 1/16* | (2006.01) |
| *C25B 1/24* | (2006.01) |
| *C25B 1/26* | (2006.01) |
| *B01D 53/14* | (2006.01) |
| *C07C 1/12* | (2006.01) |
| *C07C 29/151* | (2006.01) |
| *C07C 43/02* | (2006.01) |
| *C01C 1/04* | (2006.01) |
| *C10G 2/00* | (2006.01) |
| *C25B 1/04* | (2006.01) |
| *B01D 53/00* | (2006.01) |
| *B01D 53/02* | (2006.01) |
| *B01D 53/04* | (2006.01) |
| *C07C 1/00* | (2006.01) |
| *C07C 1/02* | (2006.01) |
| *C07C 29/15* | (2006.01) |
| *C07C 43/00* | (2006.01) |
| *C01C 1/00* | (2006.01) |
| *C01C 1/02* | (2006.01) |

(52) U.S. Cl.
CPC ............ *C07C 29/1518* (2013.01); *C07C 43/02* (2013.01); *C10G 2/50* (2013.01); *C25B 1/04* (2013.01); *C25B 1/16* (2013.01); *C25B 1/26* (2013.01); *B01D 53/04* (2013.01); *B01D 53/1475* (2013.01); *B01D 2257/504* (2013.01); *B01J 2208/00796* (2013.01)

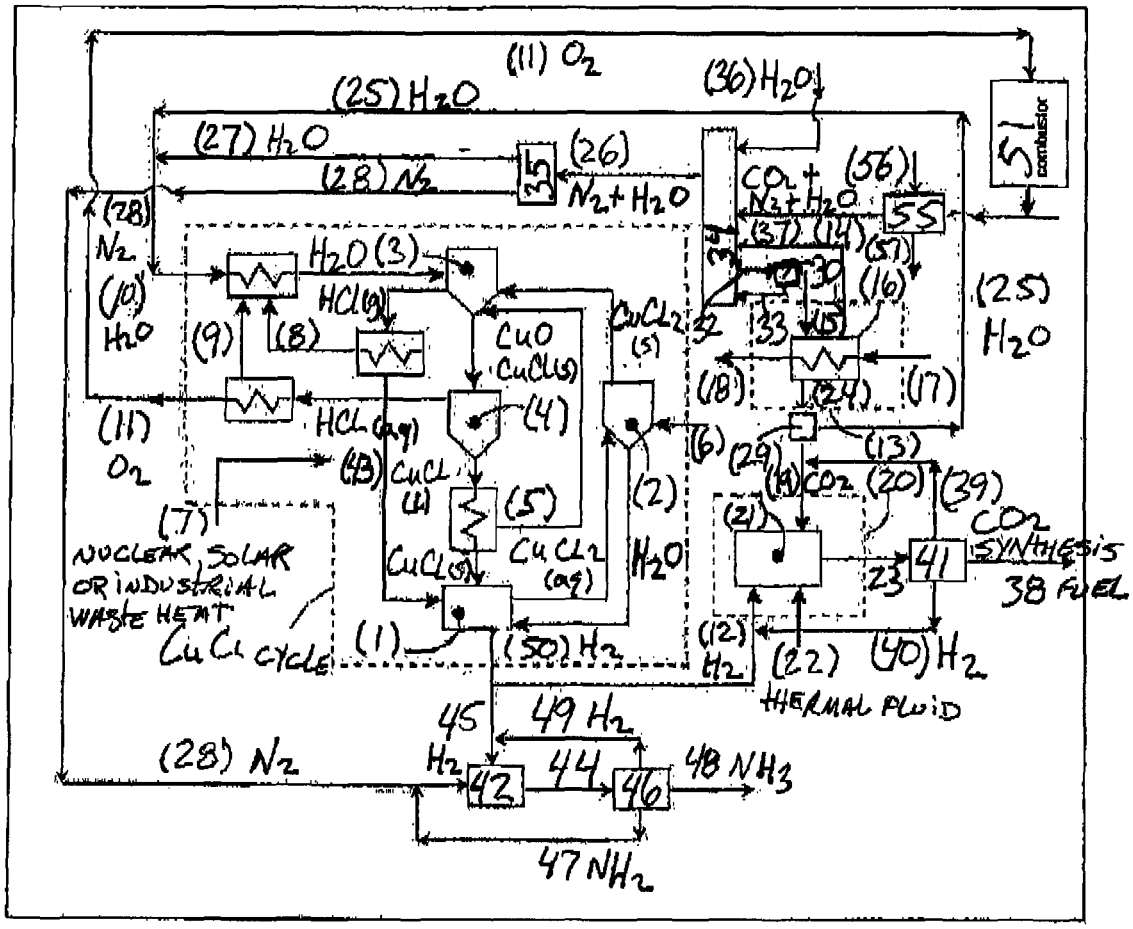
Figure 1: Schematic of the Cu-Cl cycle with $CO_2$ capture and hydrogenation (drying and hydrolysis processes of $CuCl_2$ and absorption of $CO_2$ are shown in separate apparatus)

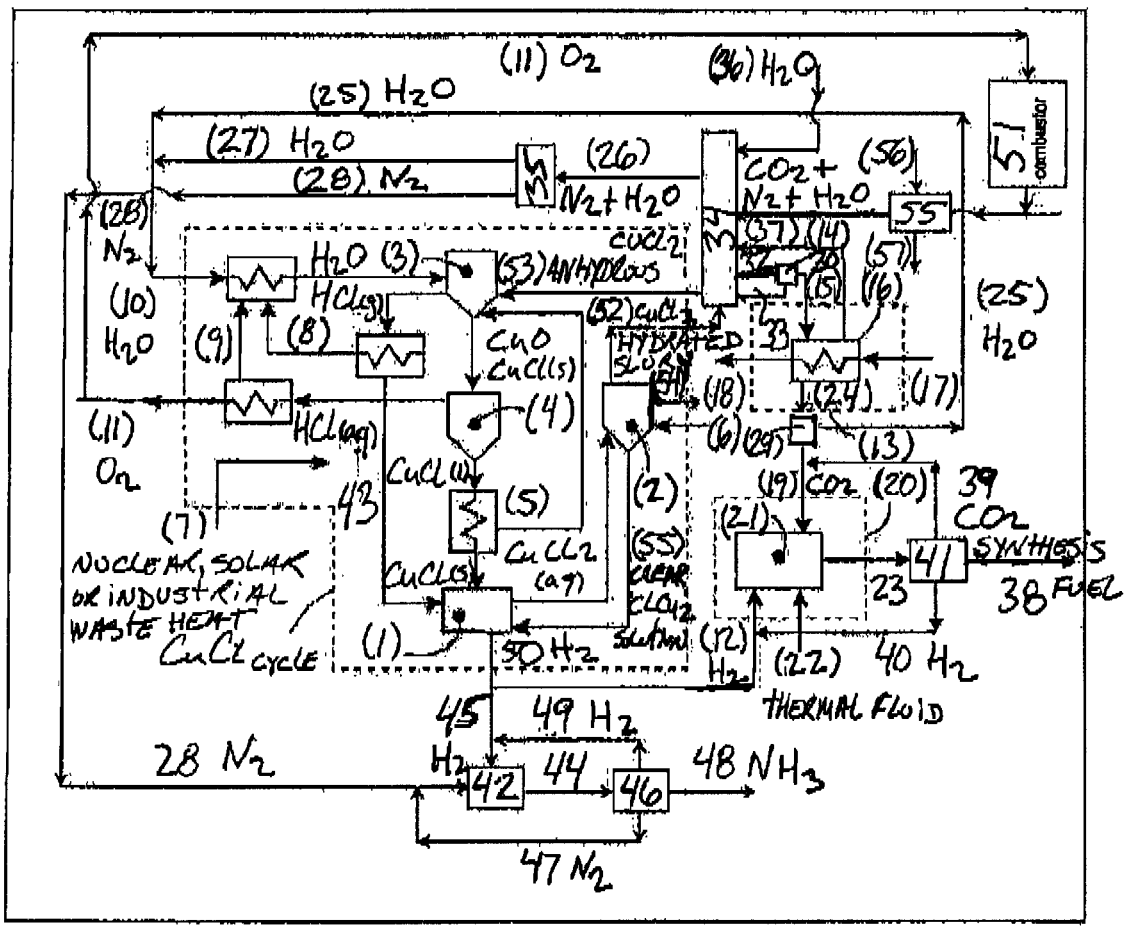
Figure 2: Schematic of the Cu-Cl cycle with $CO_2$ capture and hydrogenation (drying of $CuCl_2$ and absorption processes of $CO_2$ are implemented in the same apparatus)

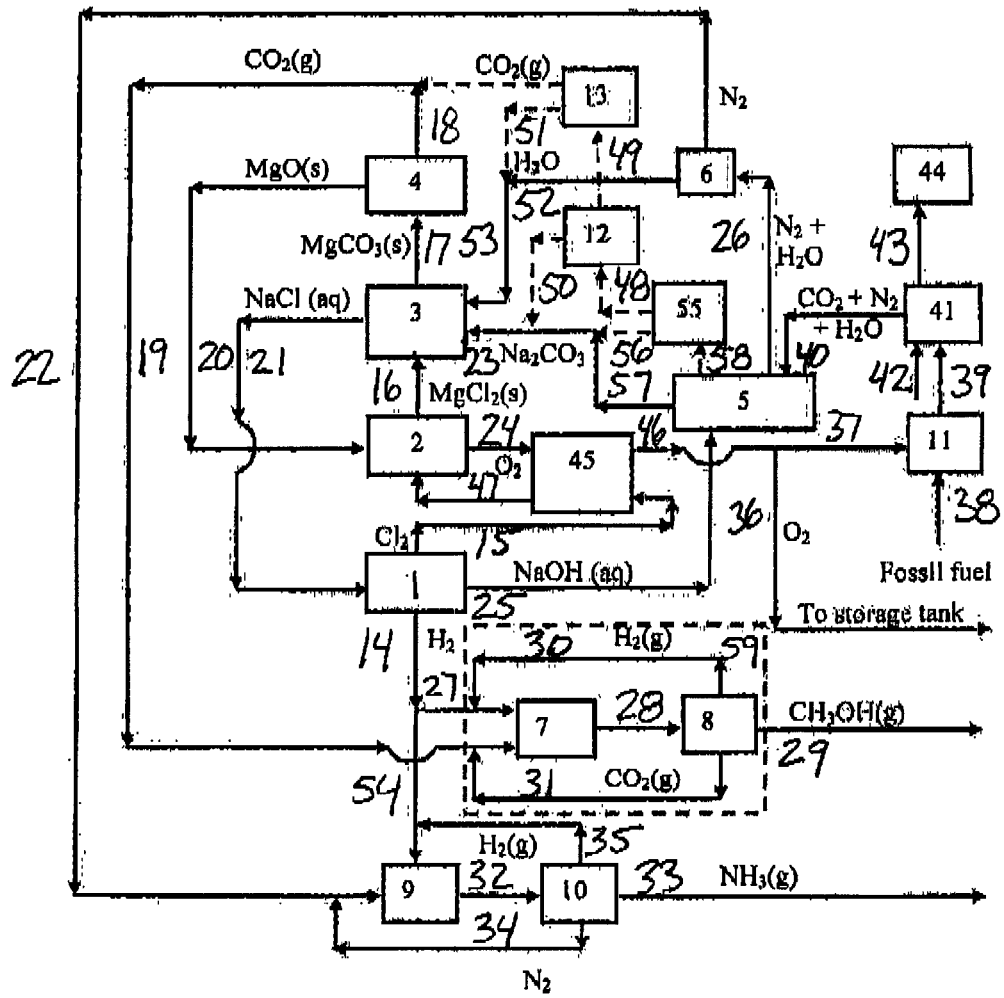
Figure 3: Mg-Cl-Na/K-CO$_2$ thermochemical cycle for synfuel production with CO$_2$ recycling and H$_2$ produciton

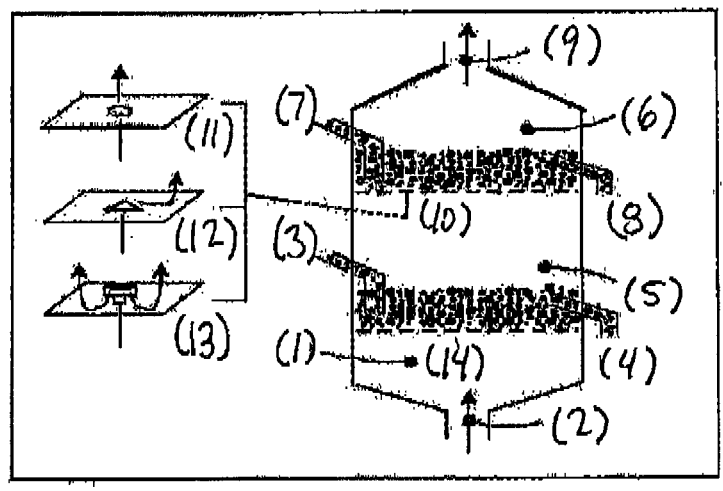
Figure 4: Schematic of a new type of two-stage fluidized/packed bed
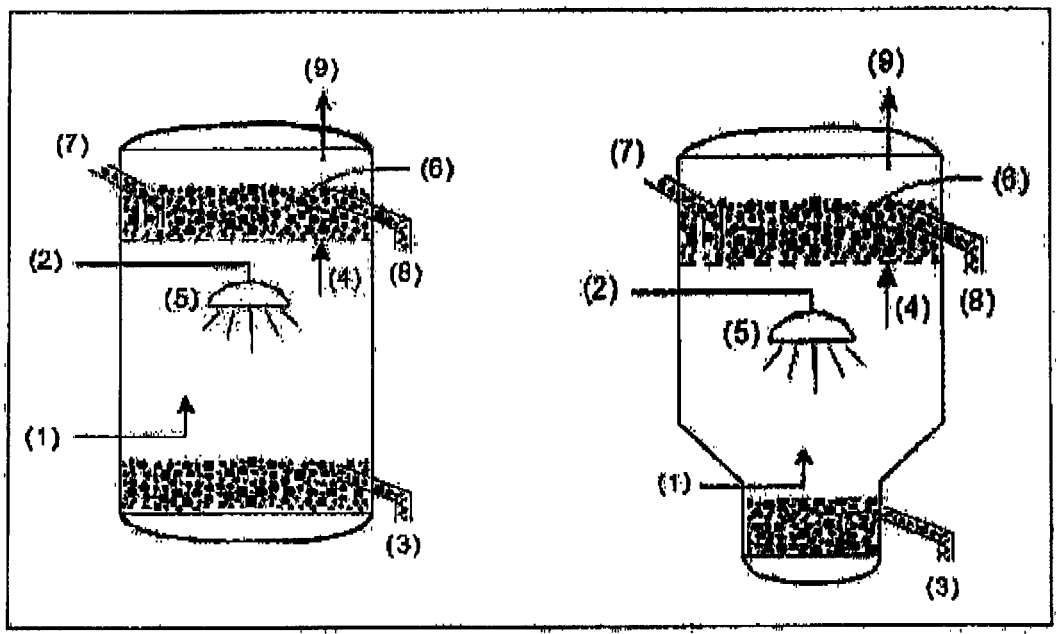
Figure 5: Schematic of a new type of hybrid two-stage spray-fluidized/packed bed reactor

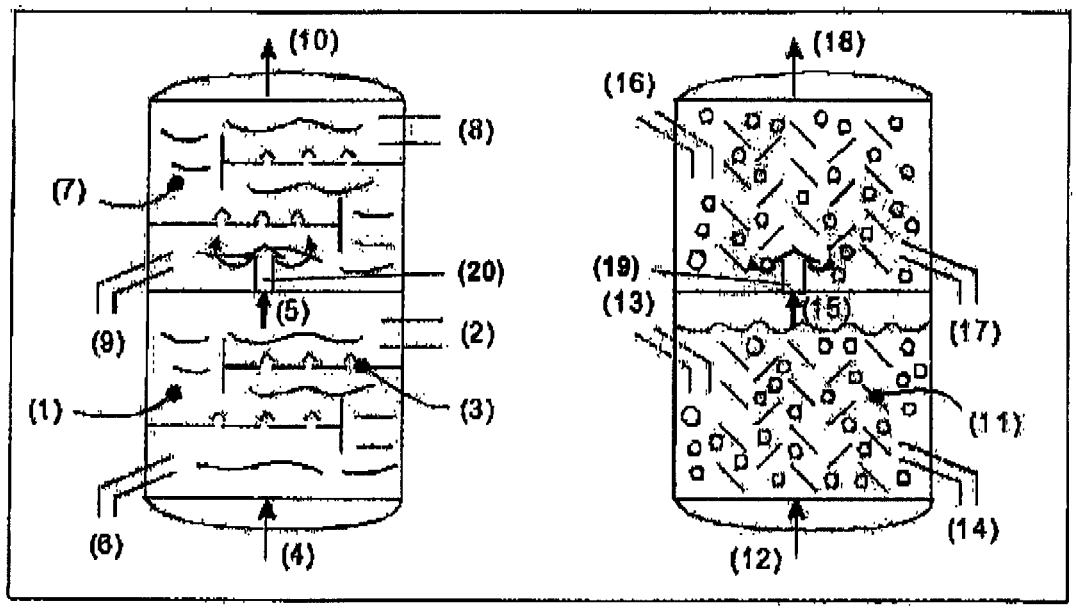
Figure 6: Schematic of a new type of two-stage wet-mode absorber
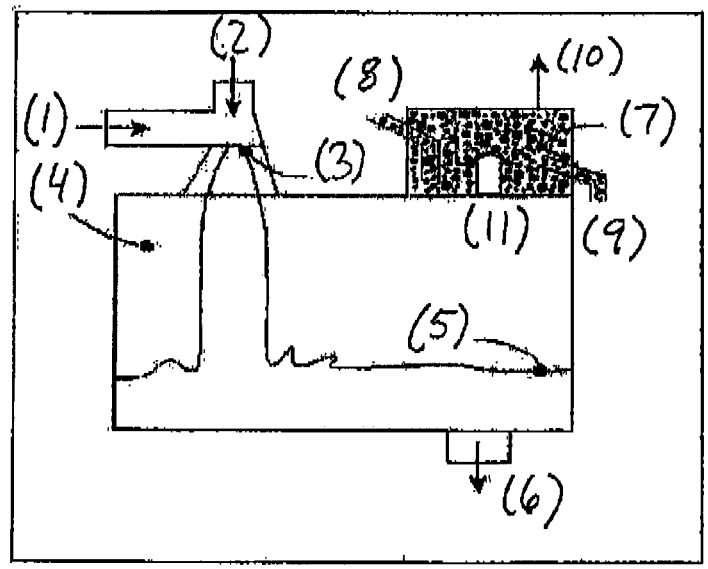
Figure 7: Schematic of a new type of hybrid two-stage absorber

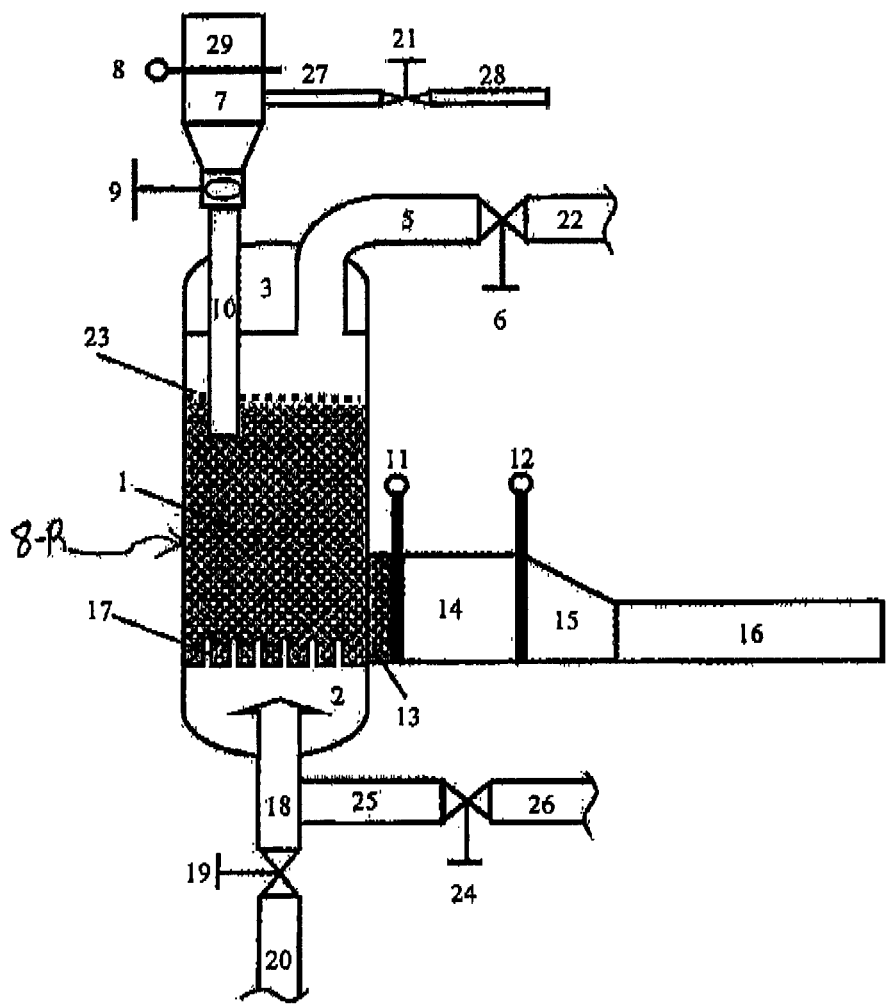
Figure 8: Schematic of a new type of catalyst packed/fluidized bed for CO₂ hydrogenation

SYSTEMS, METHODS AND DEVICES FOR THE CAPTURE AND HYDROGENATION OF CARBON DIOXIDE WITH THERMOCHEMICAL CU—CL AND MG—CL—NA/K—CO2 CYCLES

CROSS REFERENCE TO RELATED APPLICATIONS

The present application is a U.S. national phase entry of International Patent Application No. PCT/CA2013/000958. now WO 2014/071511 filed on Nov. 12, 2013, which claims priority on United States Provisional Patent Application Ser. No. 61/724,885 filed on Nov. 9, 2012 and incorporated by reference herein in its entirety.

TECHNICAL FIELD

The present disclosure generally relates to a method and system for the capture and hydrogenation of carbon dioxide. More particularly but not exclusively, the present disclosure relates. A method and system for the capture and hydrogenation of carbon dioxide with thermochemical Cu—Cl and Mg—Cl—Na/K—CO2 cycles.

BACKGROUND

Hydrogen is frequently cited to be the world's next generation fuel, since its oxidation does not emit greenhouse gases that contribute to climate change. Most major automakers are investing significantly in the development and commercialization of hydrogen vehicles. Other applications and uses of hydrogen include other transportation modes (trains, ships, utility vehicles, and so forth), as well as industries such as petrochemicals, oil sands upgrading, ammonia for fertilizer production, and others.

The predominant existing hydrogen production processes such as steam-methane reforming (SMR) use fossil fuels, so there is a need for a clean, reliable, safe, efficient and economic process for the production of hydrogen.

A known method is called the thermochemical copper-chlorine (Cu—Cl) cycle, which consists of a sequence of chemical and physical processes that decompose water into hydrogen and oxygen (see Table 1) [See Naterer, G. F., Suppiah, S., Stolberg, L., Lewis, M., Wang, Z., Daggupati, V., Gabriel, K., Dincer, I., Rosen, M. A., Spekkens, P., Lvov, L., Fowler, M., Tremaine, P., Mostaghimi, J., Easton, E. B., Trevani, L., Rizvi, G., Ikeda, B. M., Kaye, M. H., Lu, L., Pioro, I., Smith, W. R., Secnik, E., Jiang, J., Avsec, J., "Canada's Program on Nuclear Hydrogen Production and the Thermochemical Cu—Cl Cycle", International Journal of Hydrogen Energy, vol. 35, pp. 10905-10926, 20101.

TABLE 1

Steps of chemical reactions in the copper-chlorine cycle

| Step | Reaction | Temperature Range (° C.)° | Feed Output* | |
|---|---|---|---|---|
| 1 | Electrolysis: $2CuCl(aq) + 2HCl(aq) \rightarrow H_2(g) + 2CuCl_2(aq)$ | <100 | Feed: | Aqueous CuCl and HCl + V |
|  |  |  | Output: | $H_2 + CuCl_2$ (aq) |
| 2 | Concentrating: $CuCl_2(aq) \rightarrow CuCl_2(s)$ | <100 | Feed: | Slurry containing HCl and $CuCl_2$ + Q |
|  |  |  | Output | Granular $CuCl_2$ + $H_2O$ $HCl$ vapours |
| 3 | Hydrolysis: $2CuCl_2(s) + H_2O(g) \rightarrow CuO*CuCl_2(s) + 2HCl(g)$ | 400 | Feed: | Powder/granular $CuCl_2$ + $H_2O(g)$ + Q |
|  |  |  | Output: | Powder/granular $CuO*CuCl_2$ + 2HCl (g) |
| 4 | Thermolysis: $CuO*CuCl_2(s) \rightarrow 2CuCl(I) + 1/2O_2(g)$ | 500 | Feed: | Powder/granular $CuO*CuCl_2(s)$ + Q |
|  |  |  | Output: | Molten CuCl salt + oxygen |

*Q = thermal energy, V = electrical energy

Naterer et al. (2010) have outlined advances in the Cu—Cl cycle, particularly with respect to hydrogen production with Canada's Generation IV reactor, called SCWR (Super-Critical Water Reactor). Other heat sources may also be utilized for the Cu—Cl cycle, such as solar energy or industrial waste heat.

Another method is a thermochemical magnesium-chlorine-sodium/potassium-CO2 (Mg—Na/K—Cl—CO2) cycle, which consists of a sequence of chemical and physical processes that decompose water into hydrogen and oxygen (see Table 2) and at the same time capture and purify CO2.

TABLE 2

Steps of chemical reactions in a new Mg—Cl—K/Na—CO2 cycle Output

| Step | Reaction | Temperature Range (° C.) | Feed/ Output | |
|---|---|---|---|---|
| A | Electrolysis: $2NaCl(aq) + 2H_2O(l) + V = 2NaOH(aq) + Cl_2(g) + H_2(g)$ | <100 (electrolysis) | Feed: | Aqueous NaCl + V/ |
|  |  |  | Output: | Aqueous NaOH + gaseous $Cl_2$ and $H_2$ |

TABLE 2-continued

Steps of chemical reactions in a new Mg—Cl—K/Na—CO2 cycle Output

| Step | Reaction | Temperature Range (° C.) | Feed/Output | |
|---|---|---|---|---|
| B-100 | Carbonate formation:<br>2NaOH(aq) + CO2(g) =<br>Na2CO3(aq) + H20(1) + Q | <100 | Feed:<br>Output: | Aqueous NaOH + gaseous CO2/<br>aqueous Na2CO3 |
| B-101 | Carbonate formation:<br>2NaOH(s) + CO2(g) = Na2CO3(s) +<br>H20(g) + Q | <100 | Feed:<br>Output: | Solid NaOH + gaseous CO2/<br>Solid Na2CO3 |
| B-11 | Bicarbonate formation:<br>NaOH(aq) + CO2(g) =<br>NaHC03(s) + Q | <100 | Feed:<br>Output: | Aqueous NaOH + gaseous CO2/<br>Precipitated NaHC03 |
| B-12 | Na2CO3(s) + CO2(g) + H20(g) =<br>2NaHC03(s) + Q | <200 | Feed:<br>Output: | Solid Na2CO3, gaseous CO2 and H20/<br>Solid NaHC03 |
| B-13 | Na2CO3(aq) + CO2(g) + H20(1) =<br>2NaHC03(s) + Q | <200 | Feed:<br>Output: | Aqueous Na2CO3, gaseous CO2 and<br>liquid H20/<br>Solid NaHC03 |
| B-2 | Carbonate release:<br>2NaHC03(s) + Q = Na2CO3 (s) | <200 | Feed:<br>Output: | Solid Na2CO3<br>Gaseous CO2 and H20 |
| C | Precipiatation of MgC03:<br>Na2CO3(aq) + MgCl2(aq or s) →<br>MgC03(s) + 2NaCl (aq) | 300-400 | Feed:<br>Output: | Aqueous Na2CO3 and MgCl2/<br>Solid MgC03 and aqueous NaCl |
| D | Calcination<br>MgC03(s) + Q = MgO(s) +: CO2(g) | 300-600 | Feed:<br>Output: | Solid MgC03 + Q/<br>Solid MgO + gaseous CO2 |
| E | O2 production:<br>MgO(s) + Cl2(g) + Q = MgCl2(s) +<br>1/2O2(g) | 300-600 | Feed:<br>Output: | Solid MgO + gaseous Cl2 + Q/<br>Solid MgCl2 + gaseous O2 |

Q = thermal energy,
V = electrical energy
Sodium (Na) element can be replaced with potassium (K)

It has been well documented that carbon dioxide emissions to the atmosphere from fossil fuels are contributing to climate change. The post-combustion technologies of capturing and sequestering carbon dioxide in the ground are very expensive and subject to a number of technical and other challenges, including the challenge of relatively small CO2 levels due to the presence of N2, and the uncertainty about whether or not the captured CO2 will indeed remain underground for a prolonged period, removal of oxygen from the atmosphere to the ground, legal liabilities of potential leakage, etc.

A widely studied approach to reducing CO2 emissions is CO2 capture at a power plant, transport by pipeline to an underground injection site, and sequestration for long-term storage in a suitable geologic formation. [See Figueroa, J. D., Fout, T., Plasynski, S., McIlvried, H., "Advances in CO2 capture technology—The U.S. Department of Energy's Carbon Sequestration Program", International Journal of Greenhouse Gas Control, vol. 12, pp. 9-20, 2008]. CO2 capture from thermal power plants can be achieved in various ways: post-combustion capture, pre-combustion capture, and oxy-combustion. The relevant technologies for separation techniques include gas phase separation, absorption into a liquid, adsorption on a solid, hybrid adsorption/membrane systems, metal organic frameworks, ionic liquids, and enzyme-based systems. Other emerging concepts are described by Yang at al. [See Yang, H., Xu, Z., Fan, M., Gupta, R., Slimane, R. B., Bland, A. E., Wright, I., "Progress in carbon dioxide separation and capture: A review", Journal of Environmental Science, vol. 20, pp. 14-27, 2008], including chemical-looping combustion and hydrate-based separation.

An alternative to carbon recycling in the technical literature is capturing of carbon dioxide in the atmosphere by first capturing CO2 and then combining it with H2 to produce useful products such as organic chemicals, materials, synthetic fuels or carbohydrates (see examples below).

CO2+H2→CO+H2O; H298K=41.2kJ mol−1(production of carbon monoxide)  (1)

CO2+4H2→CH4+2H2O; H298K=−252.9kJmol−1 (production of methane)  (2)

CO2+3H2→CH3OH+H2O; H298K=−49.5kJ mol−1 (production of methanol)  (3)

CO2+H2→HCOOH; G273K=32.9 kJ mol−1 (production of formic acid)  (4)

Hydrogenation of carbon dioxide is an alternative to underground sequestration, as it represents a form of chemical recycling of carbon dioxide to other useful forms such as methanol and dimethyl ether [See Olah, G. A., Goeppert, A., Prakash, G. K. S., "Chemical recycling of carbon dioxide to methanol and dimethyl ether: From greenhouse gas to renewable, environmentally carbon neutral fuels and synthetic hydrocarbons", Journal of Organic Chemistry, vol. 74, no. 2, pp. 487-498, 2009]. CO2 recycling to methanol is the basis of a "methanol economy" described by Olah et al. (2009). Methods to convert CO2 to methanol include various catalytic and electrochemical conversion techniques. Methanol is a potentially viable transportation fuel for internal combustion engines (ICE) and fuel cells, as well as useful feedstock material for the production of synthetic hydrocarbons and their varied products. Recent developments in catalytic reactivity and reactor design of CO2 hydrogen processes have been described by Wang et al. [See Wang, W., Wang, S., Ma, X., Gong, J., "Recent advances in catalytic hydrogenation of carbon dioxide", Chemical Society Review, vol. 40, pp. 3703-3727, 2011].

If the sources of hydrogen and electricity generation to drive the processes are clean and sustainable, then a carbon-neutral cycle can potentially be achieved. In other words, each carbon and water molecule would be recycled over and over again, thereby not contributing to a net accumulation of carbon dioxide in the atmosphere. For example, carbon dioxide from the air and hydrogen from water would be used to produce methanol, which is a Fuel that burns to release carbon dioxide, which is again captured and recycled.

OBJECTS

An object of the present disclosure is to provide a method for the capture and hydrogenation of carbon dioxide with thermochemical Cu—Cl and Mg—Cl—Na/K—CO2 cycles.

An object of the present disclosure is to provide a system for the capture and hydrogenation of carbon dioxide with thermochemical Cu—Cl and Mg—Cl—Na/K—CO2 cycles.

SUMMARY

In accordance with an aspect thereof, the present disclosure relates to the integration of a Cu—Cl cycle, CO2 capture loop, and hydrogenation cycle.

In accordance with an aspect thereof, the present disclosure relates to the integration of an Mg—Cl—Na/K—CO2 cycle and a hydrogenation cycle.

In accordance with an aspect thereof, the present disclosure relates to processes, reactors and auxiliary devices which are used for the above integrated loops so as to produce hydrogen and oxygen, capture carbon dioxide, generate high purity N2, recover vapor from emissions/air and react the foregoing with the produced hydrogen to generate useful products such as organic chemicals, synthetic fuels, and other valuable carbon-based compounds.

In accordance with an aspect thereof, the present disclosure provides: a two-stage fluidized/packed bed reactor, as well as a hybrid two-stage spray-fluidized/packed bed reactor, a two-stage wet-mode absorber, a hybrid two-stage absorber, and a catalyst packed/fluidized bed reactor.

In an embodiment, the present disclosure relates to methods, systems and devices that produce hydrogen and capture CO2 from emissions. In an embodiment, the methods, systems and devices combine both H2 production and CO2 capture processes in forms of thermochemical cycles to produce useful products from captured CO2 such as organic chemicals, materials, synthetic fuels or carbohydrates for carbon dioxide recycling, and carbon neutral energy systems. In an embodiment, the cycles are copper-chlorine (Cu—Cl) and magnesium-chlorine-sodium/potassium cycles (Mg—Cl—Na/K—CO2). In an embodiment, one method or system comprises a Cu—Cl cycle, a CO2 capture loop, and a hydrogenation cycle. In an embodiment, the other method or system comprises an Mg—Cl—Na/K—CO2 cycle and a hydrogenation cycle.

In an embodiment, the present disclosure provides devices for hydrogen production, CO2 capture, hydrogenation, and process and equipment integration.

In an embodiment, the devices comprise:

a two-stage fluidized/packed bed that is utilized for CuCl2 hydrolysis, CuCl2 drying and dehydration processes of the Cu—Cl cycle, CO2 absorption, and O2 production with Cl2 in the Mg—Cl—Na/K cycle;

a hybrid two-stage spray-fluidized/packed bed reactor that is used for simultaneous CuCl2 drying in the Cu—Cl cycle in the spray drying chamber and CO2 absorption in the fluidzed/packed bed chamber, and the carbonation of NaOH for the capture of CO2 in the Mg—Cl—Na/K cycle;

a two-stage wet-mode absorber that serves as a scrubber system and/or CO2 absorption unit;

a hybrid two-stage absorber for undesirable gas and/or particulate scrubbing and/or CO2 absorption; and a catalyst packed/fluidized bed reactor that is used for the hydrogenation of CO2 to produce useful carbon-based products such as methanol and its derivatives, methane, and CO.

In an embodiment, the present disclosure focuses on post-combustion capture of CO2 using gas phase separation, absorption into a liquid and adsorption on solid particles.

In an embodiment, the present disclosure takes advantage of the unique thermochemical processes inherent in the Cu—Cl cycle and Mg—Cl—Na/K—CO2 cycle to implement the individual stages of CO2 hydrogenation. This involves reactor designs, processes and methods described herein.

In accordance with an aspect of the present disclosure, there is provided a system for hydrogen production, CO2 capture and production of carbon based compounds, the system comprising: a copper-chlorine (Cu—Cl) cycle; a CO2 capture loop; and a hydrogenation cycle, wherein the Cu—Cl cycle, the CO2 capture loop and the hydrogenation cycle are integrated.

In an embodiment, the system further comprises: an electrolyzer for receiving CuCl (s); a spray dryer for receiving CuCl2 (aq) from the electrolyzer; a hydrolysis reactor for receiving CuCl2 (s) from the spray dryer; a copper oxychloride decomposition reactor for receiving CuO and CuCl (s) from the hydrolysis reactor; and a CO2 capture apparatus wherein CO2 is captured from the mixture of CO2, N2, and H2O.

In an embodiment, the CO2 capture device provides water vapour and N2 to a unit for separating the water vapour and the N2 and for providing water input to the Cu—Cl cycle. In an embodiment, the CO2 capture apparatus is selected from the group consisting of a dry-mode absorber, a wet-mode absorber, a spray absorber, and any combination thereof. In an embodiment, the dry-mode absorber comprises a fluidized bed. In an embodiment, the wet-mode absorber comprises a bubble bed.

In an embodiment, the spray dryer returns H2O to the electrolyzer. In an embodiment, the spray dryer provides hydrated slurry of CuCl2 to the CO2 capture device and returns clear CuCl2 solution to the electrolyzer, the CO2 capture device providing anhydrous CuCl2 to the hydrolysis reactor.

In an embodiment, exiting CO2 and hydrogen produced from the Cu—Cl cycle enter the hydrogenation cycle to react to form a carbon-based compound. In an embodiment, hydrogen is provided from the hydrolysis reactor and CO2 is provided from the CO2 capture apparatus. In an embodiment, the hydrogen and the CO2 react in a catalytic reactor. In an embodiment, the carbon-based compound is selected from the group consisting of carbon monoxide, methane, methanol, dimethyl ether, gasoline, synthetic hydrocarbons.

In an embodiment, the system further comprises an ammonia synthesis reactor, the CO2 capture loop and Cu—Cl cycle respectively providing N2 and H2 to the ammonia synthesis reactor for producing ammonia (NH3). In an embodiment, the N2 is provided by the CO2 capture apparatus and the H2 is provided by the electrolyzer.

In an embodiment, the decomposition reactor provides for oxygen generation.

In an embodiment, solid sorbents or absorption solutions are circulated through the system and then recycled externally through a regeneration cycle that heats the sorbents/solution and releases the absorbed CO2.

In an embodiment, industrial stack emissions and steam are used as input. In an embodiment, ambient air and steam are used as input thereby providing moisture from the ambient air to supplement H2O and nitrogen from the ambient air to enhance the hydrogen production and the CO2 capture. In an embodiment, nuclear energy or waste heat are used for the Cu—Cl cycle and the CO2 capture loop.

In accordance with an aspect of the present disclosure, there is provided a system for hydrogen production, CO2 capture and production of carbon based compounds, the system comprising: a magnesium-chlorine-sodium/potassium-carbon dioxide (Mg—Cl—Na/k-CO2) cycle; and a hydrogenation cycle, wherein the Mg—Cl—Na/k-CO2 cycle and the hydrogenation cycle are integrated.

In an embodiment, the system further comprises: an electrolytic unit for producing hydrogen, chlorine gas, and sodium hydroxide (NaOH); a fluidized/packed bed for oxygen and magnesium chloride production; a precipitation vessel for receiving magnesium chloride from the fluidized/packed bed and for producing solid MgCO3 and aqueous NaCl; a calcination vessel for receiving the solid MgCO3 from the precipitation vessel and for producing high purity CO2; a CO2 absorption reactor for using the NaOH produced from the electrolytic unit as a sorbent.

In an embodiment, the oxygen produced by the fluidized/packed bed is at a high temperature and provides heat transfer to the chlorine gas produced in the electrolytic unit.

In an embodiment, precipitation vessel further produces solid MgO which is then conducted to the fluidized/packed bed as a reactant to produce O2.

In an embodiment, the system further comprises a hydrogenation reactor unit. In an embodiment, hydrogen produced from the electrolytic unit is transferred to the hydrogenation reactor unit for producing methanol (CH3OH) and for ammonia (NH3). In an embodiment, the high purity CO2 produced from the calcination vessel enters the hydrogenation reactor unit for methanol production with a hydrogenation reaction. In an embodiment, CO2 produced from the Mg—Cl—Na/K—CO2 cycle and hydrogen produced from the hydrogenation cycle enter the hydrogenation reactor unit to produce a carbon-based synthetic fuel.

In an embodiment, the aqueous NaCl produced by the precipitation vessel flows back to the electrolytic unit.

In an embodiment, CO2 in the CO2 absorption reactor reacts with the NaOH to produce Na2CO2 which is then conducted to the precipitation vessel to produce MgCO3 for CO2 release in the calcination vessel. In an embodiment, CO2 is fed to the CO2 absorption reactor in excess quantity to produce NaHCO3.

In an embodiment, the system further comprises a separator unit for receiving and separating CO2 and water vapour, the water vapour being recovered by the precipitation vessel.

In an embodiment, the system further comprises an ammonia synthesis reactor, purified N2 coming out of the CO2 absorber enters the ammonia synthesis reactor and reacts with H2 corning out of the electrolytic unit to produce ammonia (NH3).

In an embodiment, industrial stack emissions and steam are used as input. In an embodiment, ambient air and steam are used as input thereby providing moisture from the ambient air to supplement H2O and nitrogen from the ambient air to enhance the hydrogen production and the CO2 capture. In an embodiment, nuclear energy or waste heat are used for the Mg—Cl—Na/k-CO2 cycle.

In an embodiment, the system further produces a product selected from the group consisting of: carbon monoxide, methane, synthetic hydrocarbons, gasoline, derivatives of methanol, dimethyl ether, and formic acid.

In accordance with an aspect of the disclosure there is provided a two-stage fluidized/packed bed reactor for use in CuCl2 hydrolysis, CuCl2 drying and dehydration processes of a Cu—Cl cycle, and for CO2 absorption and O2 production with Cl2 in a Mg—Cl—Na/K cycle, the reactor comprising: a main body defining an inlet for allowing fluidization gases to enter the reactor and an outlet for allowing fluidization gases to exit the reactor; and at least two separate chambers defined by the main body providing two respective fluidization zones, each of the two chambers defining a respective inlet for feeding solid reactants therein and a respective outlet providing an exit for solid reactants therefrom.

In an embodiment, the two chambers comprise one lower chamber and one higher chamber.

In an embodiment, reactor inlet is at the bottom of the main body and the reactor outlet is at the top of the main body.

In an embodiment, the reactor further comprises a gas distributor plate incorporated therein. In an embodiment, the gas distributor plate is positioned at a sufficient height within the main body that enables full solid conversion and adjustment between fluidized and packed bed modes in both of the two chambers. In an embodiment, the gas distributor provides for diverting the incoming flow to then mix with the solid sorbents.

In accordance with an aspect of the disclosure, there is provided a hybrid two-stage spray-fluidized/packed bed reactor that is used for simultaneous CuCl2 drying in a Cu—Cl cycle in the spray drying chamber and CO2 absorption in a fluidized/packed bed chamber, as well as for the carbonation of NaOH for the capture of CO2 in the Mg—Cl—NaIK—CO2 cycle, the reactor comprising: a main reactor body defining a bottom and top portions thereof, the bottom portion providing for CO2-containing gas to enter the main reactor body, the top portion providing for gas to exit from the main reactor body; a fluidized/packed bed positioned within the main reactor body for absorbing CO2 and water vapour prior to the gas exiting from the top portion; and a spray nozzle for spraying droplets against the current of the incoming CO2-containing gas.

In an embodiment, the spray nozzle is positioned below the fluidized/packed bed.

In an embodiment, the bottom portion comprises a base providing an exit for particles produced during spraying of the CO2-containing gas.

In an embodiment, the main reactor body further defines an inlet and an outlet for respectively allowing solid sorbents to enter and exit the fluidized/packed bed. In an embodiment, the main reactor body comprises a lower chamber portion and an upper chamber portion, wherein the lower chamber portion comprises a diameter that is smaller than the diameter of the upper chamber portion.

In accordance with an aspect of the disclosure, there is provided a two-stage wet-mode absorber that serves as a scrubber system and/or CO2 absorption unit, the absorber comprising: a lower chamber having a bottom section thereof for gas flow to enter and move upwardly therein to a top section thereof, an inlet for liquid absorption solution to enter and progressively flow downwardly therein thereby allowing upwardly flowing incoming gas to mix with the downwardly flowing absorption solution, and an outlet for allowing absorbed gas to exit: and an upper chamber positioned above the lower chamber defining a bottom section thereof comprising gas inlets for providing fluid communication with the lower chamber thereby providing for residual gas from the lower chamber to flow upwardly therein to a top section thereof comprising a gas outlet for gas to exit out of the absorber, an inlet for an inlet for liquid absorption solution to enter and progressively flow downwardly therein thereby allowing upwardly flowing incoming gas to mix with the downwardly flowing absorption solution, and an outlet for allowing absorbed gas to exit.

In an embodiment, the lower chamber comprises a series of series of perforated surfaces with holes that permit an the upflow of gases from the bottom section of the lower chamber to the top of the section of the lower chamber through the perforated surfaces and mix with the liquid downflow, thereby enabling gas constituents from upward moving bubbles to be absorbed by the liquid absorption solution. In an embodiment, the lower chamber comprises spaced vertical inclined ledges for directing the liquid absorption solution downflow, gas bubbles flow upwardly through spaced vertical inclined ledges to mix with the liquid absorption solution.

In an embodiment, the gas inlets comprise a cap structure in order to avoid liquid within the upper chamber to enter the lower chamber.

In accordance with an aspect of the disclosure, there is provided a hybrid two-stage absorber for undesirable gas and/or particulate scrubbing and/or CO2 absorption, the absorber comprising: a first stage with a liquid solution for wet method absorption of gases; and a second stage with packed bed of solid sorbents to absorb CO2 from a gas stream or completely absorb gases not absorbed by the wet method in the first stage.

In an embodiment, the first stage comprises a mixing unit for receiving incoming CO2-containing gases and liquid to be mixed therein and spray injected into a chamber, comprising bottom and top sections thereof, so as to impact the bottom section and separate the liquid along the bottom section and air in the top section, liquid solution having absorbed particles and/or gas exits the chamber via a drain.

In an embodiment, the liquid gas mix is spray injected into the chamber via a diverging nozzle.

In an embodiment, the second stage comprises a packed bed of solid reactants for a second stage absorption of gas from the first stage passing therethrough via an inlet. In an embodiment, the packed bed of solid reactants provides for absorbing CO2. In an embodiment, the second stage defines an outlet providing for purified gas and water vapour to exit the absorber.

In an embodiment, solid reactants enter a chamber comprising the packed bed of solid reactants via an inlet and then exit therefrom via an outlet.

In an embodiment, the gas inlet comprises a cap structure for avoiding liquid or solid in the second stage to enter the first stage.

In accordance with an aspect of the disclosure, there is provided a catalyst packed/fluidized bed reactor for the hydrogenation of CO2 to produce methanol, methane, CO or their derivatives, the reactor comprising: a lower mixing chamber; one or more inlets for allowing hydrogen and CO2 to enter the mixing chamber; an upper packed/fluidized bed zone filled with catalyst particles or structures for receiving the hydrogen and CO2 mixture from the lower mixing chamber via gas channels; a double-chamber in fluid communication with the upper packed/fluidized bed zone to discharge spent solid catalysts; and a top outlet providing products produced by the reactor to exit therefrom.

In an embodiment, the reactor further comprises a pipe system with valves to control the flow rates of hydrogen and CO2 entering the reactor.

In an embodiment, the gas channels comprise top cap structures for preventing solid particles from flowing from the upper packed/fluidized bed zone down to the lower mixing chamber.

In an embodiment, a mesh is mounted to the upper packed/fluidized bed zone for avoiding breaking a catalyst structure due to stress caused by gas flow.

In an embodiment, the double-chamber comprises: a first gate for selectively allowing solid catalyst particles to flow into a first chamber from the upper packed/fluidized bed zone; and a second gate for selectively allowing solid catalyst particles to flow into a discharge vessel to be moved to a second chamber for disposal or regeneration.

In an embodiment, the reactor further comprises a replenishing in-feed assembly for replenishing the upper packed/fluidized bed zone with solid catalyst particles.

In an embodiment, the reactor further comprises a pipe system in fluid communication with the upper packed/fluidized bed zone for pressurized gas stream comprising hydrogen and CO2 to press solid particles within the reactor to flow to the upper packed/fluidized bed zone.

Other objects, advantages and features of the present disclosure will become more apparent upon reading of the following non-restrictive description of illustrative embodiments thereof, given by way of example only with reference to the accompanying drawings.

BRIEF DESCRIPTION OF THE FIGURES

Illustrative, non-restrictive embodiments of the present disclosure will now be described, by way of non-limiting example only, with reference to the attached Figures briefly described below.

FIG. 1 is a schematic illustration of the Cu—Cl cycle with CO2 capture and hydrogenation, wherein the drying and hydrolysis of CuCl2 and absorption of CO2 are implemented each in a separate apparatus;

FIG. 2 is a schematic illustration of the Cu—Cl cycle with CO2 capture and hydrogenation, wherein the drying of CuCl2 and absorption of CO2 are implemented each in the same apparatus;

FIG. 3 is a schematic illustration of the Mg—Cl—Na/K cycle with CO2 capture and hydrogenation;

FIG. 4 is a schematic illustration of a two-stage fluidized/packed bed that is utilized for CuCl2 hydrolysis, CuCl2 drying and dehydration processes of the Cu—Cl cycle, as well as for CO2 absorption, and for O2 production with Cl2 in the Mg—Cl—Na/K cycle.

FIG. 5 is a schematic illustration of a hybrid two-stage spray-fluidized/packed bed reactor that is used for simultaneous CuCl2 drying in the Cu—Cl cycle in the spray drying chamber and CO2 absorption in the fludized/packed bed chamber, as well as for the carbonation of NaOH for the capture of CO2 in the Mg—Cl—Na/K cyclel FIG. 6 is a schematic illustration of a two-stage wet-mode absorber that serves as a scrubber system and/or CO2 absorption unit;

FIG. 7 is a schematic illustration of a hybrid two-stage absorber for undesirable gas and/or particulate scrubbing and/or CO2 absorption; and FIG. 8 is a schematic illustration of a catalyst packed/fluidized bed reactor that is used for the hydrogenation of CO2 to produce useful products such as methanol and its derivatives.

DETAILED DESCRIPTION OF ILLUSTRATIVE EMBODIMENTS

Description of the Cu—Cl Thermochemical Cycle, CO2 Capture and Hydrogenation Processes FIG. 1 shows a system and method for the capture and hydrogenation of CO2 with the thermochemical Cu—Cl cycle. The drying and hydrolysis of CuCl2 and absorption of CO2 are implemented each in a separate apparatus;

The elements of the system/method of FIG. 1 that correspond to the steps of the Cu—Cl cycle shown in Table 1 are an electrochemical cell 1-1 (step 1 in Table 1), a spray dryer 1-2 (step 2), a hydrolosyis reactor in the form of a hydrolysis fluidized bed 1-3 (step 3) and a decomposition reactor 1-4 for copper oxychloride decomposition for oxygen generation (step 4).

Also provided is a casting/extrusion or spray atomization type of heat exchanger 1-5 that recovers heat from molten CuCl which solidifies upon cooling after exiting the decomposition reactor 1-4, and then transfers heat to the hydrolysis reactor 1-3 or other endothermic process in the Cu—Cl cycle. Streams 1-6 and 1-7 show the low-grade (low temperature; 100° C. and lower) and high-grade (high temperature; between 500-530° C.) points of heat input to the Cu—Cl cycle. Streams 1-8 and 1-9 refer to heat recovery processes that transfer heat from exiting HCl gas out of the hydrolysis reactor 1-3 and exiting oxygen gas out of the decomposition reactor 1-4, then transfer heat to incoming water/steam, or another endothermic process within the Cu—Cl cycle. The water input to the Cu—Cl cycle depicted in stream 1-10 comes from unit 1-35 wherein water vapour and N2 are separated. Stream 1-10 is also from unit 1-29, wherein water vapour and CO2 are separated. Water vapour and N2 come from the CO2 capture apparatus 1-34, wherein CO2 is captured from the mixture of CO2, N2, and H2O, which are the primary gases in a flue gas. The output streams of oxygen, nitrogen and hydrogen are depicted in streams 1-11, 1-28 and 1-12, respectively.

In order to capture CO2 from gases in the CO2 capture apparatus 1-34, apparatus 1-34 could be provided in the form of a dry-mode absorber such as a fluidized bed, or a wet-mode absorber such as a bubble bed and a spray absorber, or the combination thereof, depending on the composition, temperature, and pressure of the gases. Solid sorbents or absorption solutions are circulated through the units, and then recycled externally through a regeneration cycle 1-13 that heats the sorbents/solution and releases the absorbed CO2. In the CO2 absorption processes, the gas stream 1-14 containing CO2 is brought into contact with a liquid solution or solid sorbents and enters apparatus 1-34 to absorb carbon dioxide.

If the CO2 absorption process takes place in an aqueous solution in the absorber 1-34, the process is called "wet absorption" in this disclosure. After the CO2 is absorbed in apparatus 1-34, the CO2-containing sorbents (stream 1-32) enter a separator 1-30, wherein the clear solution and sludge are separated if sludge is produced. The sludge contains much more physically or chemically bonded CO2 than the clear solution. The sludge (stream 1-15) is conveyed to a CO2 stripper 1-16 and becomes heated (inflow 1-17; outflow 1-15) to release CO2 and water vapour 1-19. The clear solution (stream 1-14) is recycled back to the CO2 absorber 1-34.

The CO2 stripper 1-16 also works as a sorbent regenerator. After CO2 is stripped, the sorbents are regenerated in the meantime. Then the regenerated sorbents are returned back to the CO2 absorber 1-34 via stream 1-14.

If the CO2 capture process is implemented by solid sorbents in the absorber 1-34, the process is called "dry absorption" in this disclosure. After the CO2 is absorbed in apparatus 1-34, the CO2-containing sorbents directly enter the stripper 1-16 to release CO2 (and water vapour if the sorbents are bicarbonates). In the meantime, the sorbents are regenerated.

The wet absorption process for the capture of CO2 in apparatus 1-34 involves two major steps, in which the first step is the capture of carbon dioxide in the liquid to form carbonate precipitates or CO2-rich sorbents and the second step separates the precipitates/CO2-rich sorbents from the scrubbing liquid after the gases leave the scrubber. Depending on the flow conditions and concentration of CO2 in the gas, apparatus 1-34 may contain more than one type of structure. For example, it could include a venturi scrubber to remove entrained particulates before the gas stream enters a sorbent spray chamber. It could also include a bubble bed, wherein the gas stream is distributed in the form of bubbles to pass through a sorbent solution for an efficient CO2 absorption.

The dry absorption process for the capture of CO2 in apparatus 1-34 involves either a physical absorption or a chemical absorption process, wherein carbon dioxide reacts with or it is absorbed onto the solid sorbents. Depending on the flow conditions and concentration of CO2 in the gas, apparatus 1-34 comprises a fluidized bed, packed bed, or a moving bed. The contact and mixing pattern of the CO2 and sorbents could be counter-current, co-current, or cross-flow.

After a period of time when the sorbents absorb CO2 from the gas stream, the CO2-rich sorbents are regenerated by heating them in a separate sorbent regenerator (the stripper 1-16 which also works as a sorbent generator and is a heat exchanger), thereby either physically or chemically releasing the absorbed CO2 after heating. Depending on how the CO2 is captured, there are various other methods of regeneration such as thermochemical reactions that form intermediate compounds which are recycled.

The exiting CO2 (stream 1-19) and hydrogen produced from the Cu—Cl cycle (stream 1-12) enter the hydrogenation process (1-20) and catalytic reactor (1-21) to react to form a carbon-based compound. The synthetic compound could be methanol (CH3OH), dimethyl ether (CH3OCH3), methane (CH4), or others, depending on the catalysts and synthesis reaction conditions. The reaction is a thermal process, either endothermic or exothermic, requiring heat input or removal via stream 1-22. The synthetic fuel with unreacted CO2 and H2 enters the separator 1-41 to purify the synthetic fuel and recycle the unreacted CO2 and H2 back to the synthesis reactor 1-21 via streams 1-39 and 1-40. Then the synthetic fuel leaves the coupled system consisting of CO2 capture and Cu—Cl cycles via stream 1-38.

The coupled system consisting of CO2 capture and Cu—Cl cycles also has the capability of producing ammonia (NH3), which is useful as a fertilizer or as a fuel. The purified N2 coming out of the CO2 absorber 1-34 and water separator 1-35 enters the ammonia synthesis reactor 1-42, then reacts with H2 coming out of reactor 1-1 of the Cu—Cl cycle via stream 1-45 to synthesize ammonia. The produced ammonia and unreacted 1-12 and N2 enter the separator 1-46 for separation, then the separated H2 recycles back to the ammonia synthesis reactor 1-42 via stream 1-49, and N2 recycles re-cycles back to the ammonia synthesis reactor 1-42 via stream 1-47. The purified ammonia leaves the coupled system consisting of CO2 capture and Cu—Cl cycles via stream 1-48.

The coupled system consisting of CO2 capture and Cu—Cl cycles also has the capability of enabling an wry-combustion CO2 capture method by providing high purity oxygen for combustion to replace air. This significantly increases the CO2 capture efficiency by increasing the combustion efficiency and simultaneously avoiding or reducing the processing of N2 in air. The high purity oxygen is produced in reactor 1-4 and enters the industrial combustor 1-51 via stream 1-11. In the oxy-combustion CO2 capture, the nitrogen source for ammonia synthesis must be partly or fully external, because it is partly or fully replaced by oxygen in the combustor.

The synthetic fuels and ammonia exiting the coupled system of the CO2 capture loop and Cu—Cl thermochemical cycle can be further utilized to produce other chemicals such as amides and carbohydrates. The chemistry for these potential products does not further react or inhibit the processes of CO2 capture and H2 production. This can help industry to receive carbon offset credits and improve their environmental stewardship.

This disclosure also presents another alternative coupled system of CO2 capture and Cu—Cl thermochemical cycle to accommodate different drying methods of CuCl2.

As shown in FIG. 2, the aqueous CuCl2 exiting unit 2-1) enters a crystallizer 2-2, wherein CuCl2 hydrates, e.g., CuCl2.2H2O and CuCl2.3H2O, are precipitated out of the aqueous solution. The residual clear solution is recycled back to unit 2-1 via stream 2-55, and the hydrated CuCl2 enters unit 2-34 via stream 2-52 for dehydration. Unit 2-34 is a two-stage fluidized bed capable of performing the dehydration of hydrated CuCl2 and CO2 absorption simultaneously. Streams 2-6 and 2-54 are coolant flows that decrease the temperature of the crystallizer 2-2 for the crystallization on the basis of different solubilities of CuCl2 at different temperatures.

Description of the Mg—Cl—Na/K—CO2 Thermochemical Cycle and Hydrogenation Processes The elements of FIG. 3 that correspond to the steps of the Mg—Cl—Na/K cycle in Table 2 comprises the units discussed below.

An electrolytic unit 3-1 provides for step A to produce hydrogen, chlorine gas, and sodium hydroxide (NaOH); the hydrogen could be transferred to a hydrogenation reactor unit 3-7 and/or to unit 3-9 via stream 3-14, stream 3-27 and/or stream 3-54 for methanol (CH3OH) and/or ammonia (NH3) production. A fluidized or packed bed 3-2 is provided for oxygen and magnesium chloride (MgCl2) production in step E. The oxygen product is at a high temperature, so it is first transferred to unit 3-45 via stream 3-24 to transfer heat to the chlorine gas produced in the electrolytic unit 3-1, then conducted to combustor 3-41 to improve the combustion efficiency. The MgCl2 produced in the fluidized or packed bed unit 3-2 is conducted to unit 3-3 via stream 3-16. A precipitation vessel 3-3 provides for step C to produce solid MgCO3 and aqueous NaCl. The produced aqueous NaCl flows back to the electrolytic unit 3-1 and the solid MgCO3 enters a calcination vessel 3-4 for CO2 release. The calcination vessel 3-4, produce high purity CO2; in this unit, solid MgO is also produced, which is then conducted to the fluidized or packed bed unit 3-2 via stream 3-20 as a reactant to produce O2. A CO2 absorption reactor 3-5 uses the aqueous product NaOH produced from the electrolytic unit 3-1 as the sorbent. The NaOH flows from the electrolytic unit 3-1 to the absorption reactor 3-5 via stream 3-25.

The CO2 absorption process in the CO2 absorption reactor 3-5 is in the aqueous solution of NaOH. Hence, the process is called "wet absorption" in this disclosure. In the CO2 absorption reactor 3-5, CO2 reacts with NaOH to produce Na2CO3, which is then conducted to the precipitation vessel 3-3 via stream 3-57 to produce MgCO3 for CO2 release in the calcination vessel 3-4. The CO2 feed rate of CO2 absorption reactor 3-5 can also be operated in excess quantity to produce NaHCO3, which precipitates out of the aqueous solution of NaOH and/or Na2CO3. In this operation, the slurry of NaHCO3 enters sedimentation unit 3-55 via stream 3-58, wherein the solid NaHCO3 settles down and the clear solution comprising Na2CO3 is recovered to the precipitation vessel unit 3-3 via streams 3-56 and 3-23. Then the sludge of NaHCO3 enters unit 3-12 to decompose to Na2CO3, CO2 and water vapour, and the Na2CO3 enters the precipitation vessel unit 3-3 via stream 3-50. The CO2 and water vapour enter unit 3-13 for a separation, wherefrom the recovered water enters the precipitation vessel unit 3-3 via streams 3-51 and 3-53. The high purity CO2 enters the hydrogenation reactor unit 3-7 for methanol production. Another effluent stream of the CO2 absorption reactor 3-5 is the mixture of N2 and H2O, which is conducted to unit 3-6 via stream 3-26 for separation, then the high purity N2 could be directed to unit 3-9 via stream 3-22 for ammonia production, or directed to storage tanks for other applications.

Depending on the flow conditions and concentration of CO2 in the gas stream 3-40, the CO2 absorption reactor unit 3-5 may contain more than one type of structure. For example, it could include a venturi scrubber to remove entrained particulates before the gas stream enters a sorbent chamber. It could also include a bubble bed, wherein the gas stream is distributed in the form of bubbles to pass through a sorbent solution for an efficient CO2 absorption. Some issues may arise when particulate scrubbing and CO2 absorption are performed in the same chamber consisting of a spray or Venturi scrubber and a CO2 absorption chamber, because the particulates may be introduced into the CO2 absorption chamber.

The oxygen gas produced in the fluidized or packed bed unit 3-2 is in the temperature range of 300-600° C., as indicated by step E of Table 2. The heat carried by the oxygen gas is recovered in heat exchanger 3-45, to preheat the chlorine gas exiting the electrolytic unit 3-1 for step A of Table 2. This process increases the thermal efficiency of the coupled system consisting of the Mg—Cl—Na/K—CO2 cycle and hydrogenation loop.

The MgO produced in unit 3-4 is in the temperature range of 300-600° C., as indicated by step E of Table 2. The MgO is directly conducted to the fluidized or packed bed unit 3-2 for step E of Table 2, which occurs at the same temperature level. This arrangement avoids the preheating of MgO for step E. Thus the thermal efficiency of the coupled system consisting of the Mg—Cl—Na/K—CO2 cycle and hydrogenation loop is increased.

The high purity CO2 produced in the calcination vessel unit 3-4 is in the temperature range of 300-600° C., as indicated by step E of Table 2. The CO2 is directly conducted to the hydrogenation reactor unit 3-7 for methanol production with a hydrogenation reaction, which occurs at the same temperature level. This arrangement avoids the preheating of CO2 for step E. Thus the thermal efficiency of the coupled system consisting of the Mg—Cl—Na/K—CO2 cycle and hydrogenation loop is increased.

The CO2 stream 3-19 and hydrogen stream 3-14 produced from the Mg—Cl—Na/K cycle enter the hydrogenation reactor unit 3-7 to produce a carbon-based synthetic fuel. The synthetic fuel could be methanol (CH3OH), dimethyl ether (CH3OCH3), methane (CH4), or others, depending on the catalysts and synthesis reaction conditions. The synthetic fuel with unreacted CO2 and H2 enters the separator 3-8 to purify the synthetic fuel and recycle the unreacted CO2 and H2 back to the synthesis or hydrogenation reactor reactor unit 3-7 via streams 3-30 and 3-31. Then the synthetic fuel leaves the coupled system consisting of the Mg—Cl—Na/K—CO2 cycle and hydrogenation loop via stream 3-29.

The coupled system consisting of the Mg—Cl—Na/K—CO2 cycle and hydrogenation loop also has the capability of producing ammonia (NH3), which is a fertilizer and a fuel. The purified N2 coming out of the CO2 absorber 3-6 enters the ammonia synthesis reactor 3-9 via stream 3-22, then reacts with 1-12 coming out of the electrolytic reactor 3-1 of the Mg—Cl—Na/K—CO2 cycle via stream 3-14 and 3-54 to synthesize ammonia. The produced ammonia and unreacted H2 and N2 enter the separator 3-10 for separation, then the separated N2 recycles back to the ammonia synthesis reactor 3-9 via stream 3-34, and H2 recycles back to the ammonia synthesis reactor 3-9 via stream 3-35. The purified ammonia leaves the coupled system consisting of the Mg—Cl—Na/K—CO2 cycle and hydrogenation loop via stream 3-33.

The coupled system consisting of the Mg—Cl—Na/K—CO2 cycle and hydrogenation loop also has the capability of an oxy-combustion CO2 capture method by providing high purity oxygen for the combustion to replace air. This significantly increases the CO2 capture efficiency by increasing the combustion efficiency and simultaneously avoiding or reducing the processing of N2 in air. The high purity oxygen is produced in reactor 3-2 and enters the industrial combustor 3-11 via stream 3-37. In the oxy-combustion CO2 capture, the nitrogen source for ammonia synthesis must be partly or fully external, because it is partly or fully replaced by oxygen in the combustor.

The synthetic fuels and ammonia exiting the coupled system consisting of the Mg—Cl—Na/K—CO2 cycle and hydrogenation loop can be further utilized to produce other chemicals such as amides and carbohydrates. As previously discussed, the chemistry for these potential products does not further react or inhibit the processes of CO2 capture and H2 production.

The sodium element (Na) and the corresponding sodium compounds such as Na2CO3, NaHCO3 and NaCl described for the loop of FIG. 3 in this disclosure can be replaced with the potassium element (K) and its corresponding compounds such as K2CO3, KHCO3 and KCl, or replaced with a mixture of the same compounds of Na and K such as mixtures of NaCl and KCl, Na2CO3 and K2CO3, and NaHCO3 and KHCO3.

Description of Two-Stage Fluidized/Packed Bed for Several Major Steps of Cu—Cl Cycle, Mg—Cl—Na/K—CO2 Cycle, and CO2 Absorption This disclosure presents a two-stage fluidized/packed bed that is utilized for CuCl2 hydrolysis, CuCl2 drying and dehydration processes of the Cu—Cl cycle, and for the CO2 absorption and O2 production with Cl2 in the Mg—Cl—Na/K cycle. The fluidized/packed bed also allows for a simultaneous CO2 absorption and CuCl2 drying and dehydration operation.

As shown in FIG. 4, the fluidized/packed bed comprises two chambers (chambers 4-5 and 4-6) and hence two fluidization zones. Fluidization gases enter the fluidized bed reactor via inlet 4-2 and leave the reactor via outlet 4-9. Solid reactants are fed into the two chambers through inlets 4-3 and 4-7, and solid products exit the reactor through outlets 4-4 and 4-8.

There are a number of non-limiting advantages of using the two-stage fluidized/packed bed:

the feed rates of both gas and solid reactants can be readily controlled to meet varying H2 production and CO2 capture scales by stopping or reducing the usage of one of the fluidization zones, heat transfer can be controlled separately for the fluidization zones;

the fluidized bed can also be operated as a packed bed to meet different intake forms of solid reactants, such as pellets and fine particles;

two fluidization zones can hold two different types of sorbents separately for a more efficient CO2 absorption and heat transfer, e.g., zone (2-5) is filled with NaOH and zone (2-6) is filled with Na2CO3.

If the two-stage fluidized/packed bed is only used for the hydrolysis of CuCl2, the fluidization gas is steam or a mixture of steam and other gases, and the solid reactant is CuCl2. The hydrolysis reaction is an endothermic non-catalytic gas-solid reaction in the Cu—Cl cycle that operates between 350 and 400° C., as follows:

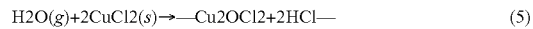

$$H_2O(g)+2CuCl_2(s)\rightarrow Cu_2OCl_2+2HCl- \tag{5}$$

The solid feed of Cu(II) chloride (CuCl2) is supplied to the hydrolysis reactor to the two fluidization zones (4-5 and 4-6) from the dried CuCl2 product of step 2 of the Cu—Cl cycle. Depending on the particle size, pressure drop, and processing quantity of solid particles, either of zone 4-5 and zone 4-6 could be operated.

The hydrolysis reaction product is cooled down to about 30° C. A gaseous mixture of steam and reaction products of HCl is condensed and sent to the downstream electrolytic hydrogen production reactor via streams (1-43) and (2-43) of the loops shown in FIGS. 1 and 2, respectively. Chlorine may be produced in an undesirable side reaction and recycled back to the hydrolysis reactor. In a current lab-scale demonstration of the hydrolysis apparatus at the University of Ontario Institute of Technology (UOIT), 30 kg/h of superheated steam at 525° C. and near atmospheric pressure is required for injection into the reactor. About 60 kW of electricity is used for process equipment requirements. Also, about 2,800 L/h of cooling water is used to cool the reactor outlet (including condensing the steam) to roughly 40° C.

If the two-stage fluidized/packed bed is only used for the absorption of CO2, the fluidization gas is CO2 or a mixture of CO2 and gases such as nitrogen and steam. The solid reactants could be NaOH, KOH, Na2CO3, or K2CO3 with the following CO2 absorption reactions:

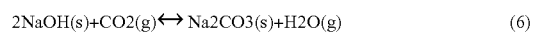

$$2NaOH(s)+CO_2(g)\leftrightarrow Na_2CO_3(s)+H_2O(g) \tag{6}$$

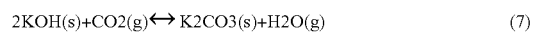

$$2KOH(s)+CO_2(g)\leftrightarrow K_2CO_3(s)+H_2O(g) \tag{7}$$

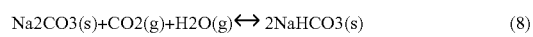

$$Na_2CO_3(s)+CO_2(g)+H_2O(g)\leftrightarrow 2NaHCO_3(s) \tag{8}$$

$$K_2O_3(s)+CO_2(g)+H_2O(g)\leftrightarrow 2KHCO_3(s) \tag{9}$$

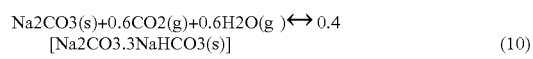

$$Na_2CO_3(s)+0.6CO_2(g)+0.6H_2O(g)\leftrightarrow 0.4[Na_2CO_3.3NaHCO_3(s)] \tag{10}$$

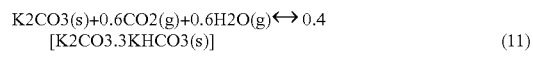

$$K_2CO_3(s)+0.6CO_2(g)+0.6H_2O(g)\leftrightarrow 0.4[K_2CO_3.3KHCO_3(s)] \tag{11}$$

The product of reaction (10) is called Wegscheider's salt and its reaction enthalpy (ΔHr) is −82 kJ/mol Na2CO3. The sorbents in zones (4-5) and (4-6) may be the same or different. If different, a recommended sorbent arrangement is that the lower zone (4-5) is filled with NaOH and/or KOH, and the upper zone (4-6) is filled with Na2CO3 and/or K2CO3. The generated Na2CO3 and/or K2CO3 with reactions (6) and (5) in the lower zone are then conveyed to the upper zone as the reactants of reactions (8)-(11). The generated steam in the lower zone also enters the upper zone to serve as part of the fluidization gases and reactants of reactions (8)-(11).

If the two-stage fluidized/packed bed is used for simultaneous CO2 absorption and CuCl2 drying and dehydration operations, the CO2 absorption process can be arranged in the lower chamber (4-5) and the dehydration of CuCl2 can be arranged in the upper chamber (4-6). This arrangement is particularly advantageous to the heat recovery from exothermic CO2 capture processes and endothermic CuCl2 dehydration. For example, when using Na2CO3 to capture the CO2, the following exothermic reaction occurs:

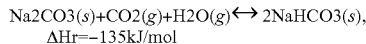

$$Na_2CO_3(s)+CO_2(g)+H_2O(g) \leftrightarrow 2NaHCO_3(s),$$
$$\Delta Hr=-135kJ/mol$$

After CO2 and H2O are absorbed out of the fluidization gases in the lower chamber (4-5), the main composition of the residual gases entering the upper chamber (4-6) includes dried N2 and other residual gases, which are viable drying gases for the dehydration of hydrated CuCl2 in the upper chamber (4-6). A typical dehydration process is given as follows:

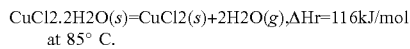

$$CuCl_2 \cdot 2H_2O(s)=CuCl_2(s)+2H_2O(g), \Delta Hr=116kJ/mol$$
$$\text{at } 85° C.$$

Since the dehydration process is endothermic, the heat released in the CO2 capture zone can be significantly recovered in the dehydration zone.

When CO2 is captured as the gas passes through the fluidized/packed bed, the sorbent is consumed during the reaction. Then the consumed sorbent is moved out of the bed reactor and CO2 is liberated when the sorbent is regenerated in loops (1-16) and (2-16) shown in FIGS. 1 and 2. The processes can be made to operate in a steady state mode in a circulating fluidized bed or transport reactor, or using multiple packed bed reactors with reaction and regeneration gas flows that alternate between the respective reactors. Solid absorption of CO2 has some useful advantages over liquid absorbers, for example, solid may be used over a wider temperature range from ambient to 700° C. and the reactor volume could be smaller.

In addition to the alkali and carbonate sorbents such as NaOH, KOH, Na2CO3 and K2CO3 listed in reactions (6)-(11), other solid CO2 sorbents could also be used. These sorbents include but are not limited to: calcined dolomite, lithium orthosilicate, and potassium treated hydrotalcite [see Harrison, D. P., "Role of Solids in CO2 capture: A Mini Review", 7th International Conference on Greenhouse Gas Control technologies, Sep. 5-9, 2004, Vancouver, Canada]. The sorbents operate by shifting the reaction equilibrium due to the removal of CO2 from the gas stream. The effectiveness of gas absorption and optimal operating conditions vary for each type of solid sorbent and CO2 composition in the gas stream.

If the two-stage fluidized/packed bed is used for the oxygen production with copper oxide (CuO) and chlorine gas (Cl2) in the Mg—Cl—Na/K—CO2 cycle, the fluidization gas is a chlorine stream or a mixture of chorine and other inert gases, while the solid reactant is CuO. The oxygen production is an exothermic non-catalytic gas-solid reaction in the Mg—Cl—Na/K cycle that operates between 300 and 600° C., as indicated by step E of Table 2.

The solid feed of CuO is supplied to the reactor to the two fluidization zones (4-5 and 4-6) from unit 3-4 via stream 3-20. Depending on the particle size, pressure drop, and processing quantity of solid particles, either of zone 4-5 and zone 4-6 could be operated. In an embodiment, fresh CuO is fed into the upper zone of the two-stage fluidized/packed bed via the inlet 4-7 and the solid product exiting outlet 4-8 enters the lower zone 4-5 via inlet 4-3 to react with fresh chlorine gas coming into zone 4-8 from inlet 4-2. This may maximize the reaction extent, which is a non-limiting advantage of using a two-stage fluidized/packed bed.

As shown in FIG. 4, a gas distributor plate 4-10 is incorporated into the fluidized/fixed bed reactor at a sufficient height that enables full solid conversion and adjustment between fluidized and packed bed modes in both the lower and higher chambers. The distributor plates comprise one of various types of plate designs, such as drilled holes 4-11, tents 4-12 or caps 4-13. In each of these plate designs, the incoming flow is diverted through the opening and then mixes with the solid sorbents. Another distributor plate 4-14 is also needed. In an embodiment, the structure and specifications are the same as 4-11, 4-12, and 4-13, although plates 4-10 and 4-14 are not the same.

If a fluidized/packed bed is adopted in the dry absorption process, the rates of flue/CO2-containing gas flows and regeneration of solid sorbents following CO2 capture are established by the flow conditions required in the lower and higher chambers for sufficient fluidization. The mass flow rates of flue/CO2-containing gases are first established to set the required fluidization regime for good mixing and heat transfer. This identifies the gas flow rate which then enters the upper section and determines the maximum flow of solid sorbents for CO2 capture. Thus the flow rates and ratios between solid sorbents and CO2 are directly correlated to the CO2 absorption rates in the fluidized bed. The spent sorbents are moved to the regenerator by a solid conveyer or other solids transport system, similar to existing technologies of other industrial CO2 capture processes that handle solid sorbents, such as CO2 emissions from coal power plants or other industrial stacks.

The present devices are also useful in other applications. The fluidized and packed beds are used to produce gasoline and other fuels, other chemicals, polymers (such as rubber, polyethylene and styrenes), coal gasification, nuclear power plants, and water and waste treatment. Also, the bubble bed is used for alkali manufacturing. Spray drying occurs in other applications such as food production (milk powder, coffee, tea, vitamins, among others), pharmaceuticals, paint pigments, ceramic materials and catalyst supports.

Thus, a number of aspects are provided in this disclosure of a two-stage fluidized/packed bed.

In one aspect of the present disclosure, the fluidized/packed bed reactor in the Cu—Cl cycle is used for:
the conversion of CuCl2 (s) to Cu2ClO2 (s) by hydrolysis;
the combination of CO2 absorption and CuCl2 drying and dehydration processes;
the chlorination of CuO with Cl2 for the Mg—Cl—NaIK—CO2 cycle; and
the absorption of CO2 with solid sorbents.

For the combination of CO2 absorption and CuCl2 drying and dehydration, CO2 is absorbed by a solid sorbent in the first stage in the lower chamber, followed by a second section that dries and dehydrates CuCl2 in the upper chamber. This system can therefore use industrial stack emissions and steam as the input, thereby providing a method of CO2 capture and water recovery from industrial sources. Alternatively, the system can utilize ambient air and steam as the input, thereby providing moisture from air to supplement H2O, nitrogen from air to enhance the CuCl2 dehydration and CO2 capture. Although the CO2 concentration in ambient air is much lower than industrial stack emissions, CO2 capture from ambient air is advantageous because it can be more selectively dispersed geographically and not limited to the location of an industrial site. If ambient air is used for the loop, then the reactor size is much larger than using a flue gas.

Description of a Hybrid Two-Stage Spray-Fluidized/Packed Bed Reactor

The present disclosure provides a hybrid two-stage spray-fluidized/packed bed reactor that is used for a simultaneous CuCl2 drying (see Table 1; step 2 in the Cu—Cl cycle) in the spray drying chamber and CO2 absorption in the fluidized/packed bed chamber, as well as for the carbonation of NaOH for the capture of CO2 in the Mg—Cl—NaIK—CO2 cycle (see Table 2; steps B-100, B-11, B-12, and B-13).

As illustrated in FIG. 5, in the first possible configuration, a CO2-containing gas (air or other gases) enters from the bottom 5-1, counter-current to the sprayed droplets, then the produced particles exit from the base 5-3 of the chamber. The produced gas in the spray chamber flows upwards past the spray nozzle 5-5 until it reaches an upper chamber 5-4, and flows through a fluidized/packed bed 5-6 of solid sorbents. The solid sorbents such as Na2CO3 and K2CO3 entering at inlet 5-7 and exiting at outlet 5-8 absorb CO2 and water vapour from the upcoming gas stream before the gas exits from the top 5-9. The CO2 absorption process can be any of the reactions (8)-(10). In an embodiment, the liquid to gas ratios and pressure drops lie between 10-20 gal/1,000 ft$^3$ (1-2 inches water) for the spray operation.

The hybrid two-stage spray-fluidized/packed bed reactor is used for the CuCl2 drying. The process of water removal from aqueous Cu(II) chloride is expressed by: 2CuCl2 (aqueous or slurry)+2CuCl2 (s) (see Table I; step 2 of the Cu—Cl cycle) after the HCl is stripped out of the aqueous solution. Through a spray drying process, water is removed from the aqueous solution or slurry of CuCl2 that exits the electrolysis cell to produce solid CuCl2(s), which is then supplied to the hydrolysis reactor (step 3) to produce copper oxychloride (Cu2OCl2) and HCl gas. Spray drying is one of the possible methods for water removal, through atomization of the CuCl2 solution into small droplets on the order of a few hundred microns. Although the drying process is energy-intensive, it can be accomplished at a relatively low temperature with low-grade "waste" heat to improve the cycle's thermal efficiency. The drying heat requirement typically increases from 1 to 5 times for slurry compared to solution feed, respectively, depending on the CuCl2 concentration. According to the processing scale, there could be multiple nozzles for the spray chamber.

The spray drying process is conducted at temperatures ranging from room temperature to about 250° C. The operating pressure is near atmospheric. The process flow occurs as follows: CuCl2 solution is pumped from a holding tank to the spray dryer, where it is atomized with compressed air. Air for drying is heated and injected into the spray drying chamber, where it contacts the solution droplets causing evaporation of moisture and production of particulate. At temperatures below about 100° C., the expected product could be either anhydrous CuCl2 or "hydrated CuCl2" such as CuCl2.H2O and CuCl2.2H2O, in particulate form.

If the hybrid two-stage spray-fluidized/packed bed reactor is used for the simultaneous CuCl2 drying and CO2 capture, then the two-stage unit serves as unit 1-34 in the loop of FIG. 1. In the first possible configuration, a CO2-containing gas (air or other gases) enters from the bottom 5-1, counter-current to the sprayed droplets (aqueous CuCl2 entering at 5-2), then the produced CuCl2 particles exit from the base of the chamber 5-3. The produced gas in the spray chamber flows upwards past the spray nozzle 5-5 until it reaches an upper chamber at 5-4, and flows through a fluidized/packed bed 5-6 of solid sorbents (entering at 5-7; exiting at 5-8) such as Na2CO3 and K2CO3, which absorb CO2 and water vapour from the upcoming gas stream before the gas exits the outlet 5-9. The CO2 absorption process can be any of the reactions (8)-(10). The dried CuCl2 particles exit from the base of the chamber 5-3.

To minimize the entrainment of CuCl2 particles in the drying gas stream, the lower chamber must be high enough and the gas stream speed should be lower than the terminal velocity of the CuCl2 particles.

If utilizing the hybrid two-stage spray-fluidized/packed bed reactor for the simultaneous CuCl2 drying and CO2 capture, then the two-stage unit serves as unit 2-34 in the loop of FIG. 2. After CO2 is captured and a portion of water vapour is absorbed, the major composition of the effluent gases out of the upper fluidized/fixed zone of the two stage unit is nitrogen and residual water vapour, which form the stream 2-26. The dried cupric chloride coming out of the outlet 5-3 forms the stream 2-53, which serves as the reactant of the hydrolysisreactor 2-3. The CO2-rich sorbents coming out of the outlet 5-8 enters the loop 2-16 for sorbent regeneration and CO2 release.

A second potential configuration in FIG. 5 includes a lower chamber with a smaller diameter than the larger chamber. This is to reduce the speed of CuCl2 particles with an expansion section so that the CuCl2 particles entering the upper chamber can be minimized.

In addition to the alkali and carbonate sorbents such as NaOH, KOH, Na2CO3, and K2CO3 listed in reactions (6)-(11), other solid CO2 sorbents could also be used for the single unit combining a two-stage spray dryer and a fluidized/packed absorber. These sorbents include but are not limited to: calcined dolomite, lithium orthosilicate, and potassium treated hydrotalcite [see Harrison, D. P., "Role of Solids in CO2 capture: A Mini Review", 7th International Conference on Greenhouse Gas Control technologies, Sep. 5-9, 2004, Vancouver, Canada]. The sorbents operate by shifting the reaction equilibrium due to the removal of CO2 from the gas stream. The effectiveness of gas absorption and optimal operating conditions vary for each type of solid sorbent and CO2 composition in the gas stream.

To minimize the entrainment of Na2CO3 and NaOH particles in the drying gas stream, the lower chamber must be high enough and the gas speed should be lower than the terminal velocity of the CuCl2 particles. The entrained solid particle may clog the inlet 5-4.

If utilizing the hybrid two-stage spray-fluidized/packed bed reactor for the Mg—Cl—Na/K—CO2 cycle, in the first possible configuration, a CO2-containing gas (air or other gases) enters from the bottom 5-1, counter-current to the sprayed droplets (aqueous NaOH entering at 5-2) for the carbonation reaction of step A of Table 2. The produced Na2CO3 particles are mixed with unreacted dry NaOH exit from the base of the chamber 5-3, and then they enter the upper fluidized/packed bed chamber through inlet 5-7. The gas in the spray chamber continues to flow upwards past the spray nozzle 5-5 until it reaches an upper chamber at 5-4. It flows through a fluidized/packed bed 5-6 of the solid Na2CO3 and NaOH, which react with CO2 water vapour from the upcoming gas stream before the gas exits the outlet 5-9. The CO2 absorption process in the upper fluidized/packed bed is primarily the reaction indicated by steps B-12 and B-101 of Table 2. The produced solid particles of NaHCO3 and Na2CO3 exit from the base of the chamber 5-3.

If utilizing the hybrid two-stage spray-fluidized/packed bed reactor for the CO2 absorption with Mg—Cl—N/K—CO2 cycle, then the two-stage unit serves as unit 3-5 in the loop of FIG. 3. After CO2 is captured and a portion of water vapour is absorbed, the major composition of the effluent gases out of the upper fluidized/fixed zone of the two stage unit is nitrogen and residual water vapour, which form the stream 3-26. The solid NaHCO3 and Na2CO3 coming out of the outlet 5-3 forms the stream 3-58.

A second configuration in FIG. 5 includes a lower chamber with a smaller diameter than the larger chamber. This is to reduce the ascension speed of Na2CO3 and NaOH particles with an expansion section so that the particles entering the upper chamber can be minimized.

Thus, there are several aspects of the disclosure inherent in this hybrid unit. For the coupled system of a Cu—Cl cycle with CO2 capture, a new spray dryer is proposed to convert CuCl2 (aqueous or slurry) to CuCl2(s) by spray drying in the first stage, followed by a second section that absorbs CO2 by a fluidized/packed bed of solid sorbents, separated physically from the bed of CuCl2(s) particles formed by the drying process in the Cu—Cl cycle. For the Mg—Cl—N/K—CO2 cycle, the spray dryer converts NaOH (aq) to Na2CO3 in the first stage, followed by a second stage to convert Na2CO3 into NaHCO3 in the fluidized/packed bed. The configuration may be extended to other forms of combined spray and fixed/packed bed systems such as vane type cyclonic towers or multiple tube cyclones in the spray chamber, in conjunction with other variations of the fluidized/packed bed absorber such as a fiber bed, moving bed, cross-flow, or grid-packed bed working with solid particles and gases, while the spray system involves liquid droplets and gases. Drying gas streams from the ambient air or industrial stack emissions could be used as the input, although low humidity drying gases are preferred since moisture in the gas stream would reduce the drying rate.

Description of Two-Stage Wet-Mode Absorber for Gas Scrubbing and/or CO2 Absorption The present disclosure provides a two-stage wet-mode absorber that can serve as a scrubber system and/or CO2 absorption unit.

A scrubber system refers to an air pollution control device that removes particulates and/or toxic gases from industrial exhaust streams so as to facilitate the CO2 capture. The scrubber systems have traditionally referred to air pollution systems that use liquid to wash unwanted pollutants from a gas stream. Scrubbers are one of the primary devices that control gaseous emissions. To minimize the contamination of CO2 sorbents, the scrubber must remove particulates and/or other selected toxic gases such as SO2 from the emissions before the exhaust stream enters the downstream CO2 absorption unit.

If the two-stage wet-mode absorber serves as a scrubber system for the coupled system of the Cu—Cl cycle and CO2 capture, the industrial exhaust gases or ambient air are passed through the scrubber 1-55 or 2-55, then the exit gases including CO2, nitrogen, steam and other trace gases form the stream 1-37 or 2-37 to enter the CO2 absorption unit 1-34 or 2-34. The scrubber liquid flows into the scrubber via stream 1-56 or 2-56, and then exits via stream 1-57 or 2-57 for regeneration or appropriate disposal. A two-stage scrubber is depicted in FIG. 6, which uses a liquid solution to remove the particulates and other toxic gases out of the emissions.

If the two-stage wet-mode absorber serves as a CO2 absorption unit for the coupled system of the Cu—Cl cycle and CO2 capture, the absorber serves as unit 1-34. The regenerated liquid CO2 sorbents such as aqueous Na2CO3 enter unit 1-34 via stream 1-14, and then enter unit 1-30 to separate the clear solution from the sedimentation (sludge) of NaHCO3. Then the sludge enters the regeneration unit 1-24 via stream 1-15 to regenerate the sorbents and in the meantime, release the absorbed CO2 and other absorbed gases into stream 1-24.

If the two-stage wet-mode absorber serves as a scrubber system for the Mg—Cl—Na/K—CO2 loop, the industrial exhaust gases or ambient air carrying CO2 is passed through the scrubber 3-41, then the exit gases including CO2, nitrogen, steam and other trace gases form the stream 3-40 to enter the CO2 absorption unit 3-5. The scrubber liquid is aqueous solution of NaOH, which flows into the scrubber via stream 3-42 to implement step B-100 of Table 2, and then exit via stream 3-43 to unit 3-44 for regeneration or appropriate disposal. A two-stage scrubber is depicted in FIG. 6, which uses a liquid solution to remove the particulates and other toxic gases out of the emissions.

In FIG. 6, two possible configurations are illustrated which use liquid solutions to absorb gas constituents of interest and/or particulates from the exhaust stream. In the first configuration (lower section of the scrubber; 6-1), a liquid scrubber solution enters chamber 6-1 via inlet 6-2 and flows progressively downwards over a series of perforated surfaces 6-3 with holes that permit an upflow of gases from the bottom 6-4 to the top of the section 6-5. This allows an incoming gas flow 6-4 from the bottom to pass through the perforated section and mix with the liquid downflow, thereby enabling the gas constituents from the upward moving bubbles to be absorbed by the liquid solution (exits at 6-6), which is then transferred out to a regenerator or disposal section. Then the regenerated solution is returned back to the scrubber to operate a cyclic process. To avoid the liquid of the upper zone entering the lower zone, the top of the gas inlets 6-19 and 6-20 has a cap structure.

Depending on the amount of gases of interest and/or the particulates to be absorbed, the upper chamber 6-7 can be operated similarly or differently. For example, the absorption liquid in the upper chamber can be the same as that used in the lower chamber, or different if necessary. The absorption liquid can be either a fresh absorption liquid or the effluent liquid coming out of the lower chamber via outlet 6-6. The absorption liquid enters the inlet 6-8 and absorbs residual gas constituents of interest and/particulates, then leaves the upper chamber via 6-9 to be transferred to the upper chamber, a regenerator, or a disposal section according to the absorption requirements.

A similar configuration is shown in the second schematic of FIG. 6. However, rather than a sequence of surfaces with perforated openings, a different arrangement is used to enhance the contact between gas bubbles and the absorbing liquid solution. A number of spaced vertical inclined ledges 6-11 are used to direct the liquid downflow, through which the gas bubbles flow upwards to mix with the liquid (gas inflow from bottom at 6-12). The absorption solution enters at 6-13 and exits at 6-14. Similar arrangements are used for the liquid inflow, outflow and regeneration as the prior above configuration. The gas enters the upper section at 6-15; absorption solution enters at 6-16, exits with absorbed CO2 at 6-17, and final exiting gas at 6-18. Another possible configuration is to use plastic rings, solid spheres, or other obstructions in the liquid solution that enhance mixing as the gas flows through the liquid solution. These are some of the various possible configurations that can be used in each of the two absorber sections of the scrubber system.

Depending on the amount of gases of interest and/or the particulates to be absorbed, the upper chamber can be operated similarly or differently. For example, the absorption liquid in the upper chamber can be the same as that used in the lower chamber, or different. The absorption liquid can be either a fresh absorption liquid or the effluent liquid coming out of the lower chamber via outlet 6-14. The absorption liquid enters the inlet 6-16 and absorbs residual gas constituents of interest and/or particulates, then leaves the upper chamber via 6-17 to be transferred to the a regenerator or a disposal section.

If the two-stage wet-mode absorber serves as a CO2 absorption unit for the coupled system of the Cu—Cl cycle and CO2 capture, monoethanolamine (MEA) is a commonly used liquid in industry to absorb CO2 from industrial stack emissions. MEA absorption processes are existing commercial technologies that bring a gas stream containing CO2 into contact with an MEA solution in an absorber. Carbon dioxide is absorbed by the solution. The MEA solution reacts with CO2 bubbles dispersed within the liquid to form MEA carbomate, which is a CO2-rich solution that is then sent to the stripper 1-16, heated to release almost pure CO2, then recycled back to the absorber.

Other absorption liquids include aqueous solutions of NaOH, KOH, Na2CO3, Na2CO3, and combination therein. The majority of the CO2 captured liquid will lead to the formation of carbonate and/or bicarbonate. The carbonate and/or bicarbonate are sent to unit 1-16 for sorbent regeneration and CO2 release. The formation of bicarbonate is more preferable than carbonate, because the release temperature of CO2 from the bicarbonates is much lower than carbonates, and the regeneration of CO2 sorbents is easier also.

If the two-stage wet-mode absorber serves as the CO2 absorption unit for steps B-100 and B-11 of Mg—Cl—Na/K—CO2 cycle, the aqueous solution of NaOH is used for both the lower and upper chambers of the two structures shown in FIG. 6 to produce an aqueous solution of Na2CO3, which is then conducted to unit 3-3 via streams 3-57 and 3-23 of the loop shown in FIG. 3. In this operation, the reaction is step B.

If a large excess amount of CO2 is absorbed, then both the lower and upper chambers can be used to support step B-11 to produce slurry of solid NaHCO3 and aqueous Na2CO3, which is then conducted to unit 3-55 via stream 3-58 of the loop shown in FIG. 3.

A third option is that the lower chamber can be used to produce aqueous solution of Na2CO3 for step B-100 of Table 2, and then aqueous Na2CO3 is conducted to the upper chamber to continue the absorption to produce the slurry of solid NaHCO3 and aqueous Na2CO3 for step B-13, which is then conducted to unit 3-55 via stream 3-58 of the loop shown in FIG. 3.

There are a number of non-limiting advantages of using the two-stage wet-mode absorber:
- the feed rates of both the gas stream and liquid sorbents can be readily controlled to meet the varying 1-12 production and CO2 capture scales by stopping or reducing the usage of one of the two absorption zones;
- the heat transfer can be controlled separately in the two absorption zones; and
- the two absorption zones can hold two different types of sorbents separately for a more efficient CO2 absorption and heat transfer, e.g., the lower zone is filled with aqueous solution of NaOH and/or KOH, wherein the reactions indicated by equations (6) and (7) occur; the upper zone is filled with Na2CO3 and/or K2CO3 generated from the lower zone, wherein the reactions indicated by equations (8)-(10) take place.

Depending on the desired liquid flow rates, undesirable gas/particulate removal rates and CO2 capture rates, the wet-mode absorber may be extended to other configurations such as a perforated plate, impingement plate scrubber, or horizontal plate (baffle) scrubber.

The two-stage wet-mode absorber can also serve as a scrubber and a CO2 absorber simultaneously, i.e., all of the product gases except N2 and water vapour are removed through a single unit. Then for the Cu—Cl cycle, the absorber serves as unit 1-34, and unit 1-55 does not need to exist in the loop of FIG. 1. In the operation, the lower scrubber section removes selected and trace gases and particulates from the industrial exhaust streams. After the completion of the lower stage scrubbing in section 6-1, the gas passes into the upper section 6-7 wherein a different liquid solution like an MEA solution or another liquid sorbent (enters at 6-8; exits at 6-9) is used in the upper zone to absorb CO2 from the incoming gas stream. Subsequently, the purified N2 and water vapour leaves through a single exit at the top of the chamber.

For the Mg—Cl—Na/K—CO2 cycle, the absorber serves as unit 3-5, and unit 3-41 does not need to exist in the loop of FIG. 3. In the operation, the lower scrubber section removes the selected and trace gases and particulates from the industrial exhaust stream. After the completion of the lower stage scrubbing in section 6-1, the gas passes into the upper section 6-7 wherein aqueous solution of NaOH produced from unit 3-1 is used in the upper zone to absorb CO2 from the incoming gas stream. Subsequently the purified N2 and water vapour leaves through a single exit at the top of the chamber.

Flow Conditions and Transport Processes of the Two-Stage Wet-mode Absorber

The gas and vapour collection in the wet scrubbers occurs by absorption. Contact between the mixture of gases and liquid occurs wherein one or more of the constituents of the gas will dissolve into the liquid. The rate of transfer of the soluble constituents from the gas to the liquid phase is determined by the equilibrium thermodynamic state and diffusion processes on each side of the liquid-gas interface. Key operating parameters of the scrubbing process are the velocity/gas flow rate, liquid/gas ratio and pressure drop. It is crucial to stay within the design conditions. For example, in a packed bed or tray tower, excessively low gas flows might cause plugged packing in the absorber, fan problems, or an undesired increase in the liquid flow through the tower. Conversely, excessive gas flow might indicate packing failure or insufficient liquid flow, so the liquid/gas flow ratios must be effectively balanced.

In an embodiment, the liquid to gas ratios and pressure drops for the wet scrubbers d lie between 1-4 gal/1,000 ft$^3$ (1-10 inches water) for each absorption zone. If the pressure drop exceeds these recommended values, this can lead to plugging or an undesired increase in the gas or liquid flow rate, whereas an insufficient pressure drop would have undesirable effects such as channeling through the scrubber due to inadequate liquid distribution or damage to support plates that causes packing materials to fall through the plates.

Distributor plates are located at the interface between the counter-current flows of liquid and gas. Various types of distributor plates may be used such as perforated plates, inclined ledges, orifice pan distributor, lateral pipe distributor, collector/distributor, support grids or gas injection support plates. The distributor plates are covered with a mesh or fine screen, which distribute and regulate the gas flow. Support grids are connected onto the distributor plates. A gas injection support grid is a device to hold the packing. It holds the packing and contains openings with a slotted or perforated plate that is positioned so as to allow increased gas flow.

In an orifice type distributor, a flat surface is fabricated with holes for both gas upflow and liquid downflow. The gas flows upwards through a chimney type structure which can be circular or rectangular. The liquid collects on a deck or weir to a certain level and then falls through holes or drip tubes. A collector/redistributor system is similar with a deck and chimneys, except a collector is used under the packed bed section to collect liquid and assist in flow mixing and redistribution, as well as caps to prevent water falling from the packing from bypassing the collector. In contrast, a lateral pipe distributor is a pressure driven distributor where the liquid is delivered through orifices in branch pipes. These types of distributors would be most effective for cases with high liquid flow rates and limited space availability. However, they are not recommended if there is a significant volume of particulate or suspended solids due to the potential for plugging of the orifices.

Thus, the disclosure provides a wet-mode absorption system for a scrubber system and/or a $CO_2$ absorption system for the coupled system of the Cu—Cl cycle and $CO_2$ capture loop, and also for the Mg—Cl—Na/K—$CO_2$ cycle. The scrubber system is used for the removal of undesirable particulates and other gases such as $SO_2$ emitted from an industrial plant. This system then utilizes industrial stack emissions and steam as the input to the Cu—Cl cycle and the Mg—Cl—Na/K—$CO_2$ cycle, or else ambient air and steam as the input. If ambient air is used for the loop, then the reactor size is much larger than using a flue gas.

Description of a Hybrid Two-Stage Absorber for Scrubbing and/or $CO_2$ Absorption The disclosure provides another hybrid two-stage absorber for undesirable gas and/or particulate scrubbing and/or $CO_2$ absorption.

As shown in FIG. 7, a venturi-type absorption system is depicted with a liquid solution in the first stage, and a packed bed of solid sorbents in the second stage is used to absorb $CO_2$ from the gas stream or completely absorb the gases that are not readily absorbed by the wet method in the first stage.

In the first stage, incoming $CO_2$-containing gases 7-1 and liquid 7-2 are mixed and injected through a diverging nozzle 7-3 into a chamber 7-4 as a jet flow that impacts at the base and separates the liquid along the bottom and air in the top section (liquid free interface at 7-5). The liquid solution has absorbed dust and/or gas and it then exits through a drain 7-6 at the base. The gas stream will then flow out through the upper section of the chamber and pass through a packed bed of solid reactants 7-7 for a second stage absorption. The solid reactants enter at inlet 7-8 and then exit from 7-9 to leave the two-stage unit.

In an embodiment, the liquid to gas ratios and pressure drops lie between 5-8 gal/1,000 ft$^3$ (10-70 inches water of pressure drop) for the venturi type scrubber.

If the hybrid two-stage absorber serves as a scrubber system for particulates and/or undesirable gases for the coupled system of the Cu—Cl hydrogen cycle and $CO_2$ capture loop, then the scrubber works as unit 1-55 or 2-55 of FIGS. 1 and 2. The Industrial exhaust gases or heated ambient air is passed through the scrubber 1-55 or 2-55, then the exit gases including $CO_2$, nitrogen, steam and other trace gases, form the stream 1-37 or 2-37 to enter the $CO_2$ absorption unit 1-34 or 2-34. The scrubber liquid flows into the scrubber via stream 1-56 or 2-56, and then exits via stream 1-57 or 2-57 for regeneration or appropriate disposal.

If the hybrid two-stage absorber only serves as a $CO_2$ absorption unit for the Cu—Cl cycle, the absorber serves as unit 1-34 of the loop shown in FIG. 1. The regenerated liquid $CO_2$ sorbents such as aqueous $Na_2CO_3$ enters unit 1-34 via stream 1-14, and then enters unit 1-30 to separate the clear solution from sedimentation (sludge) of $NaHCO_3$. Then the sludge enters the regeneration unit 1-24 via stream 1-15 to regenerate the sorbents and in the meantime release the absorbed $CO_2$ and other absorbed gases into stream 1-24. The clear solution returns to the unit 1-34 via stream 1-33.

The hybrid two-stage absorber can also serve as a scrubber and a $CO_2$ absorber simultaneously in a single unit, i.e., all of the product gases except $N_2$ and water vapour are removed through a single unit. Then for the Cu—Cl cycle, the absorber serves as unit 1-34 of the loop shown in FIG. 1, and unit 1-55 does not need to exist in the loop of FIG. 1. In the operation, the lower scrubber section removes selected and trace gases and particulates from the industrial exhaust stream. After the completion of the first stage scrubbing in section 7-4, the gas passes into the second stage 7-7 via the gas inlet 7-11. $CO_2$ is absorbed by the sorbents such as solid $Na_2CO_3$ and NaOH in the second stage by a packed bed. Subsequently the purified $N_2$ and water vapour leaves through a single exit 7-10 at the top of the chamber.

If the hybrid two-stage absorber serves as a scrubber system for particulates and/or undesirable gases for the Mg—Cl—Na/K—$CO_2$ loop, then the scrubber works as the unit 3-41 of FIG. 3. The industrial exhaust gases or heated ambient air is passed through the scrubber 3-41, and then the exit gases including $CO_2$, nitrogen, steam and other trace gases form the stream 3-40 to enter the $CO_2$ absorption unit 3-5. The scrubber liquid flows into the scrubber via stream 3-42, and then exits via stream 3-43 for regeneration or appropriate disposal.

Separate chambers could be used for the $CO_2$ capture operations. However, there are a number of non-limiting advantages of combining two-part chambers rather than separating the units:
  it reduces the equipment, hardware, cost, complexity and flow losses;
  it performs $CO_2$ capture under any flow conditions of the packed bed and venturi scrubber since the reactant supply rates of sorbents are adjusted based on the required $CO_2$ absorption rate and water intake rate required by the Cu—Cl cycle for hydrogen production;
  the $CO_2$ capture capabilities can be adapted into the hydrogen production devices without adversely impacting their throughputs;
  it enhances the "green" capabilities of the Cu—Cl cycle by additionally capturing $CO_2$ and recycling water; and
  it allows equipment manufactures to expand their products into the $CO_2$ capture and water recovery market.

Some issues may arise when particulate scrubbing and $CO_2$ absorption are performed in the same chamber consisting of a venturi scrubber and a packed bed, particularly liquid water may be introduced to the gas-solid fluidized bed. This is addressed by carefully controlling the flows of $CO_2$-containing gas and water flow rates.

The apparatus of this disclosure therefore provides a system and method of hybrid two-stage absorption for undesirable gas and particulate scrubbing and/or $CO_2$ absorption. This method and system can utilize ambient air as the input, or industrial emissions with $CO_2$ that can be captured and subsequently processed further into useful products as described previously. The two-stage absorber involves a combined system of a venturi type scrubber and a packed bed. Depending on the desired CO2 capture and scrubbing capacity, the venturi type scrubber may be modified to include other configurations such as an orifice scrubber, flooded disc, plumb bob, movable blade, radial flow or variable rod system. The reactants in the second stage chamber can also be a liquid, for example, MEA solutions or aqueous Na2CO3. To avoid the liquid or solid of the upper zone entering the lower zone, the top of the gas inlet 7-11 is a cap structure.

Description of a Packed/Fluidized Bed Reactor for Hydrogenation

A catalyst packed/fluidized bed reactor can be used for the hydrogenation of CO2 to produce useful products such as methanol and its derivatives. Either heterogeneous catalysts or homogeneous catalysts work for the reactor, depending on the stability, activity, the likeliness of handling and reuse of the catalyst, as well as lower reactor dimensions for large capacity production.

The most direct route to methanol from CO2 is the catalytic regenerative conversion of CO2 with hydrogen. This reaction has been known and commercially practiced for decades in industry. Some of the earliest methanol plants in the U.S. in the 1920s used carbon dioxide for methanol production. Since that time, more efficient catalysts based on metals and their oxides, such as the combination of copper and zinc oxide, have been developed. The synthesis of methanol from CO2 and H2 has also been demonstrated on a pilot scale in Japan, where a 50 kg CH3OH/day production was achieved. A liquid-phase methanol synthesis process was developed, which allows a CO2 and H2 conversion to methanol of about 95%.

In current industry, methanol is usually produced by the reaction of CO2 and H2 contained in the syngas on the catalyst's surface. To be converted to methanol, some of the syngas needs to first undergo a water gas shift reaction to give additional H2 and form CO2. The formed CO2 then reacts with hydrogen to produce methanol. In this disclosure, the feed gas to the hydrogenation reactor is different from those used in current industry. The feed gases consisting of hydrogen and CO2 are supplied from the coupled system of Cu—Cl cycle and CO2 capture loop, or from the Mg—Cl—Na/K—CO2 cycle.

The schematic illustration of the packed/fluidized bed reactor 8-R is shown in FIG. 8.

Hydrogen flowing from pipe 8-20 enters the reactor via the inlet 18, and CO2 flowing from pipe 8-25 enters the reactor via the inlet 8-25. The flow rates of hydrogen and CO2 are controlled with valves 8-19 and 8-24, respectively. The hydrogen and CO2 enter the mixing chamber 8-2 and then flow upward into the packed/fluidized bed zone 8-1, which is filled with the solid catalyst particles or structures. To improve the gas distribution and prevent solid particles from flowing down to the lower mixing chamber 8-2, the gas channels 8-17 have conical caps on the top. If the catalyst is fixed onto a structure for a packed bed catalytic reaction, mesh 8-23 is set to avoid breaking the catalyst structure due to the stress caused the gas flow. The produced methanol, methane, CO or their derivatives and unreacted hydrogen and CO2 leave the reactor via the outlet 8-5.

At the bottom of the packed/fluidized bed, 8-14 and 8-15 form a double-chamber to discharge spent solid catalysts. In the operation, gate 8-11 is first opened to allow the solid catalyst particles flow into the chamber 8-14, and in the meantime, gate 8-12 is closed. After chamber 8-14 is filled with solid particles, gate 8-11 is closed. Then gate 8-12 is opened to allow the solid particles to flow into the discharge vessel 8-15, and the particles are then moved to chamber 8-16 for disposal or regeneration.

To replenish the catalyst, gate 8-8 is opened to allow chamber 8-7 to be filled with fresh catalyst particles, and valves 8-9 and 8-21 are closed. After chamber 8-7 is filled with catalyst particles, gate 8-8 is closed and gates 8-9 and 8-21 are opened. A pressurized gas stream consisting of hydrogen and CO2 is applied in pipe 8-27 to press the solid particles to flow down into the zone 8-1 via pipe 8-10.

Depending on the desirable products, residence time, mixing quality, and the number of reaction steps for the hydrogenation of CO2, the reactor can be adjusted to operate in a packed bed mode or fluidized bed mode. The ratio of hydrogen to CO2 can be controlled with the valves 8-19 and 8-24 so as to assist the formation of different products.

For the coupled system of the Cu—Cl cycle and CO2 capture loop, the hydrogen is produced in the CuCl/HCl electrolyzer (unit 1-1 in FIG. 1, unit 2-1 in FIG. 2), then hydrogen is conducted to inlet 8-20 to enter the mixing chamber 8-2, wherein H2 is mixed with CO2 that is captured in loop 1-13 or 2-13 coupled to the Cu—Cl cycle. The captured CO2 enters the reactor via the inlet 8-26. The mixture of hydrogen and CO2 enters the catalyst packed/fluidized bed reactor 8-R (at 8-2). The produced methanol exits the reactor via the outlet 8-22, which is stream 1-23 of the loop shown in FIG. 1, or stream 2-23 of the loop shown in FIG. 2. The reactor serves as units 1-21 and 2-21 for the loops shown in FIGS. 1 and 2, respectively.

For the Mg—Cl—Na/K—CO2 cycle, the hydrogen is produced in the electrolyzer of NaCl aqueous solution (unit 3-1 in FIG. 3), then hydrogen is conducted to inlet 8-20 to enter the mixing chamber 8-2, wherein H2 is mixed with CO2 that is released from units 3-4 and 3-13 of the loop shown in FIG. 3. The captured CO2 enters the reactor via the inlet 8-26. The mixture of hydrogen and CO2 enters the catalyst packed/fluidized bed reactor 8-R (at 8-2) and produced methanol exits the reactor via the outlet 8-22, which is stream 3-28 of the loop shown in FIG. 3. The reactor 8-R serves as the unit 3-7 in FIG. 3.

Thus, this aspect of the disclosure provides to hydrogenation of captured CO2 with the hydrogen produced from the Cu—Cl cycle or Mg—Na/K—CO2 cycle and produce methanol or other derivatives in a catalyst fixed/fluidized bed reactor. A derivative example is dimethyl ether, which is an important intermediate raw material for many chemical industries such as leather, rubber, fibers, materials, organic chemicals and carbohydrates. Alternatively, the system is e used to produce carbon monoxide and methane and their derivatives.

Scope of the Integration of the Cu—Cl Cycle, CO2 Capture and Hydrogenation Processes As schematically shown in FIGS. 1 and 2 and the systems described in the above sections, when these above systems are coupled, form a closed system which integrates the Cu—Cl cycle with the CO2 capture loop and the hydrogenation process, thereby taking inputs of water and industrial emissions/air, to produce outputs of hydrogen, CO2, and other useful carbon-based products described earlier.

The operation of the thermochemical copper-chlorine (Cu—Cl) cycle described in this disclosure does not depend on the presence of the CO2 capture loop. This provides good flexibility to adjust the CO2 capture scale. The Integration layouts illustrated in FIGS. 1 and 2 can therefore be applied to other thermochemical cycles as well, such as sulfur-based cycles under development in the USA, Japan, Korea, and China. This includes the incorporation of a non-Cu—Cl thermochemical cycle, CO2 capture loop 1-16, and the hydrogenation loop 1-20 to enable a large enclosed loop to operate in a steady-state cyclic manner. Alternatively, it includes the Incorporation of a non-Cu—Cl thermochemical cycle, CO2 capture loop 2-16, and the hydrogenation loop 2-20.

The closed system can utilize nuclear energy and waste heat from a nuclear power plant for the Cu—Cl cycle, to capture CO2 and produce useful products from the captured CO2. Alternatively, the system can utilize solar energy as the heat input to the Cu—Cl cycle, as well as part of a hybrid system for electricity generation needed for CO2 capture and hydrogenation processes.

Scope of the Integration of the Mg—Cl—Na/K—CO2 Cycle and Hydrogenation Processes As schematically shown in FIG. 3 and described in the previous sections, the Mg—C1-N/K—CO2 cycle is capable of producing hydrogen and capturing CO2 simultaneously with a single cycle. When the cycle is coupled with a hydrogenation loop, a large closed system is formed, thereby taking inputs of water and industrial emissions/air, to produce outputs of hydrogen and other useful products described earlier.

The operation of the Mg—Cl—N/K—CO2 cycle described in this disclosure depends on the presence of the CO2 capture process, as described in FIG. 3 and table 2. Therefore, the production scale of 1-12 is proportional to the CO2 capture scale. The Mg—Cl—NaIK—CO2 cycle can utilize nuclear energy and waste heat from a nuclear power plant for the Mg—Cl—N/K—CO2 cycle, to capture CO2 and produce useful products. Alternatively, the system can utilize solar energy as the heat input to the Mg—Cl—N/K—CO2 cycle, as well as part of a hybrid system for electricity generation needed for the cycle and hydrogenation processes.

The various features described herein can be combined in a variety of ways within the context of the present description so as to provide still other embodiments. It is to be understood that the present description is not limited in its application to the details of construction and parts illustrated in the accompanying drawings and described hereinabove. The description is capable of other embodiments and of being practiced in various ways. It is also to be understood that the phraseology or terminology used herein is for the purpose of description and not limitation. Hence, although the present description has been provided hereinabove by way of non-restrictive illustrative embodiments thereof, it can be modified, without departing from the scope, spirit and nature of the disclosure and appended claims.

What is claimed is:

1. A system for hydrogen production, CO2 capture and production of carbon based compounds, the system comprising:
   a copper-chlorine (Cu—Cl) cycle;
   a CO2 capture loop;
   a hydrogenation cycle;
   wherein the Cu—Cl cycle, the CO2 capture loop and the hydrogenation cycle are integrated;
   an electrolyzer for receiving CuCl (s);
   a spray dryer for receiving CuCl2 (aq) from the electrolyzer;
   a hydrolysis reactor for receiving CuCl2 (s) from the spray dryer;
   a copper oxychloride decomposition reactor for receiving CuO and CuCl (s) from the hydrolysis reactor; and
   a CO2 capture apparatus wherein CO2 is captured from the mixture of CO2, N2, and H2O,
   wherein the spray dryer provides hydrated slurry of CuCl2 to the CO2 capture device and returns clear CuCl2 solution to the electrolyzer, the CO2 capture device providing anhydrous CuCl2 to the hydrolysis reactor.

2. A system according to claim 1, wherein the CO2 capture device provides water vapour and N2 to a unit for separating the water vapour and the N2 and for providing water input to the Cu-Cl cycle.

3. A system according to claim 1, wherein the CO2 capture apparatus is selected from the group consisting of a dry-mode absorber, a wet-mode absorber, a spray absorber, and any combination thereof.

4. A system according to claim 1, wherein the spray dryer returns H2O to the electrolyzer.

5. A system according to claim 1, wherein exiting CO2 and hydrogen produced from the Cu—Cl cycle enter the hydrogenation cycle to react to form a carbon-based compound.

6. A system according to claim 5, wherein hydrogen is provided from the hydrolysis reactor and CO2 is provided from the CO2 capture apparatus.

7. A system according to claim 1, wherein the carbon-based compound is selected from the group consisting of carbon monoxide, methane, methanol, dimethyl ether, gasoline, synthetic hydrocarbons.

8. A system according to claim 1, further comprising an ammonia synthesis reactor, the CO2 capture loop and Cu—Cl cycle respectively providing N2 and H2 to the ammonia synthesis reactor for producing ammonia (NH3).

9. A system according to claim 8, wherein the N2 is provided by the CO2 capture apparatus and the H2 is provided by the electrolyzer.

10. A system according to claim 1, wherein the decomposition reactor provides for oxygen generation.

11. A system according to claim 1, wherein solid sorbents or absorption solutions are circulated through the system and then recycled externally through a regeneration cycle that heats the sorbents/solution and releases the absorbed CO2.

12. A system according to claim 1, wherein industrial stack emissions and steam are used as input.

13. A system according to claim 1, wherein ambient air and steam are used as input thereby providing moisture from the ambient air to supplement H2O and nitrogen from the ambient air to enhance the hydrogen production and the CO2 capture.

14. A system according to claim 1, wherein nuclear energy or waste heat are used for the Cu—Cl cycle and the CO2 capture loop.

15. A system for hydrogen production, CO2 capture and production of carbon based compounds, the system comprising:
   a magnesium-chlorine-sodium/potassium-carbon dioxide (Mg—Cl—Na/K—CO2) cycle; and
   a hydrogenation cycle,
   wherein the Mg—Cl—Na/K—CO2 cycle and the hydrogenation cycle are integrated.

16. A system according to claim 15, wherein industrial stack emissions and steam are used as input.

17. A system according to claim 15, wherein ambient air and steam are used as input thereby providing moisture from the ambient air to supplement H2O and nitrogen from the ambient air to enhance the hydrogen production and the CO2 capture.

18. A system according to claim 15, wherein nuclear energy or waste heat are used for the Mg—Cl—Na/K—CO2 cycle.

19. A system according to claim 15, further producing a product selected from the group consisting of: carbon monoxide, methane, synthetic hydrocarbons, gasoline, derivatives of methanol, dimethyl ether, and formic acid.

20. A system according to claim 15, further comprising:
an electrolytic unit for producing hydrogen, chlorine gas, and sodium hydroxide (NaOH);
a fluidized/packed bed for oxygen and magnesium chloride production;
a precipitation vessel for receiving magnesium chloride from the fluidized/packed bed and for producing solid MgCO3 and aqueous NaCl;
a calcination vessel for receiving the solid MgCO3 from the precipitation vessel and for producing high purity CO2;
a CO2 absorption reactor for using the NaOH produced from the electrolytic unit as a sorbent.

21. A system according to claim 20, wherein the oxygen produced by the fluidized/packed bed is at a high temperature and provides heat transfer to the chlorine gas produced in the electrolytic unit.

22. A system according to claim 20, wherein the precipitation vessel further produces solid MgO which is then conducted to the fluidized/packed bed as a reactant to produce O2.

23. A system according to claim 20, further comprising a hydrogenation reactor unit, wherein hydrogen produced from the electrolytic unit is transferred to the hydrogenation reactor unit for producing methanol (CH3OH) and /or ammonia (NH3).

24. A system according to claim 20, further comprising a hydrogenation reactor unit, wherein the high purity CO2 produced from the calcination vessel enters the hydrogenation reactor unit for methanol production with a hydrogenation reaction.

25. A system according to claim 20, wherein the aqueous NaCl produced by the precipitation vessed flows back to the electrolytic unit.

26. A system according to claim 20, wherein CO2 in the CO2 absorption reactor reacts with the NaOH to produce Na2CO2 which is then conducted to the precipitation vessel to produce MgCO3 for CO2 release in the calcination vessel.

27. A system according to claim 20, wherein CO2 is fed to the CO2 absorption reactor in excess quantity to produce NaHCO3.

28. A system according to claim 20, further comprising a separator unit for receiving and separating CO2 and water vapour, the water vapour being recovered by the precipitation vessel.

29. A system according to claim 20, wherein CO2 produced from the Mg—Cl—Na/K—CO2 cycle and hydrogen produced from the hydrogenation cycle enter the hydrogenation reactor unit to produce a carbon-based synthetic fuel.

30. A system according to claim 20, further comprising an ammonia synthesis reactor, purified N2 coming out of the CO2 absorber enters the ammonia synthesis reactor and reacts with H2 coming out of the electrolytic unit to produce ammonia (NH3).

* * * * *